| United States Patent [19] | [11] Patent Number: 4,861,785 |
| Stokbroekx et al. | [45] Date of Patent: Aug. 29, 1989 |

[54] BENZOXAZOL-AND BENZOTHIAZOLAMINE DERIVATIVES, USEFUL AS ANTI-ANOXIC AGENTS

[75] Inventors: Raymond A. Stokbroekx, Beerse; Marcel G. M. Luyckx, Geel; Frans E. Janssens, Bonheiden, all of Belgium

[73] Assignee: Janssen Pharmaceutica N.V., Beerse, Belgium

[21] Appl. No.: 786,895

[22] Filed: Oct. 11, 1985

Related U.S. Application Data

[63] Continuation-in-part of Ser. No. 677,412, Dec. 3, 1984, abandoned.

[51] Int. Cl.⁴ .................. A61K 31/38; A61K 31/40; A61K 31/395; C07D 413/12

[52] U.S. Cl. .................. 514/321; 514/299; 514/301; 514/302; 514/318; 514/322; 514/367; 514/375; 546/114; 546/115; 546/117; 546/162; 546/193; 546/194; 546/199; 548/159; 548/161; 548/164; 548/222

[58] Field of Search ............... 546/198, 114, 115, 162, 546/117, 193, 194, 199; 548/159, 222, 161, 164; 514/299, 301, 302, 318, 321, 322, 367, 375

[56] References Cited

U.S. PATENT DOCUMENTS

4,038,396 6/1977 Shen et al. .................. 546/115
4,477,276 10/1984 Willms et al. .................. 546/115

OTHER PUBLICATIONS

Goodman et al., The Pharmacological Basis of Therapeutics, 6 Ed., p. 28.

*Primary Examiner*—Mary C. Lee
*Assistant Examiner*—J. Richter

[57] ABSTRACT

Benzoxazol-and benzothiazolamine derivatives having anti-anoxic properties which compounds are useful in the treatment of anoxia.

18 Claims, No Drawings

BENZOXAZOL-AND BENZOTHIAZOLAMINE DERIVATIVES, USEFUL AS ANTI-ANOXIC AGENTS

REFERENCE TO RELATED APPLICATIONS

This is a continuation-in-part of our co-pending application Ser. No. 677,412 filed Dec. 3, 1984, now abandoned.

BACKGROUND OF THE INVENTION

In U.S. Pat. No. 4,219,559 there are described a number of N-heterocyclyl-4-piperidinamines, wherein said heterocyclyl is imidazole being condensed with benzene or pyridine, which compounds are useful as antihistaminic agents.

The compounds of the present invention containing an analogous heterocyclyl radical differ therefrom by the fact that said heterocyclyl is oxazole or thiazole being condensed with benzene or pyridine and by their unexpected anti-anoxic properties.

Description of the Preferred Embodiments

This invention is concerned with novel benzothiazol- and benzoxazolamine derivatives which structurally may be represented by the formula

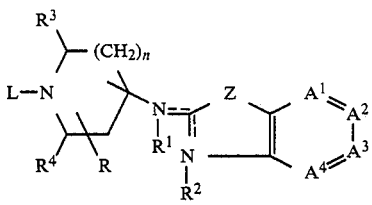

the pharmaceutically acceptable acid addition salts and the possible stereochemically isomeric forms thereof, wherein: $-A^1=A^2-A^3=A^4-$ is a bivalent radical having the formula

| | |
|---|---|
| $-CH=CH-CH=CH-$ | (a); |
| $-N=CH-CH=CH-$ | (b); |
| $-CH=N-CH=CH-$ | (c); |
| $-CH=CH-N=CH-$ | (d); or |
| $-CH=CH-CH=N-$ | (e); | wherein one or two hydrogen atoms in the radical $-A^1=A^2-A^3=A^4-$ may, each independently from each other, be replaced by halo, $C_{1-6}$ alkyl, hydroxy, $C_{1-6}$ alkyloxy, or trifluoromethyl;

Z is O or S;
n is 0 or the integer 1;
R is a member selected from the group consisting of hydrogen, $C_{1-6}$ alkyl, hydroxy and $C_{1-6}$ alkyloxy;
$R^1$ or $R^2$ is hydrogen, $C_{1-6}$ alkyl, or aryl $C_{1-6}$ alkyl; the dotted line between the nitrogen atom bearing $R^1$, the interjacent carbon atom and the nitrogen atom bearing $R^2$ indicating that a double bond exists between the nitrogen bearing $R^1$ and said interjacent carbon atom, in which case $R^1$ is absent, or a double bond exists between the interjacent carbon and the nitrogen bearing $R^2$, in which case $R^2$ is absent; and wherein said interjacent carbon atom is the carbon atom positioned between the nitrogen bearing $R^1$ and the nitrogen bearing $R^2$;

$R^3$ or $R^4$ are both hydrogens or $R^3$ and $R^4$ combined may form a bivalent radical of formula $-CH_2-CH_2-$;
L is a member selected from the group consisting of $C_{1-12}$ alkyl, substituted $C_{1-6}$ alkyl, aryl $C_{2-6}$ alkenyl, $C_{3-6}$ cycloalkyl, substituted $C_{3-6}$ cycloalkyl, a radical of formula

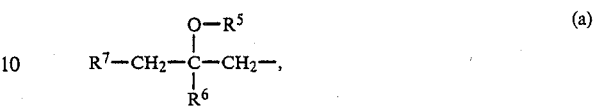

and a radical of formula

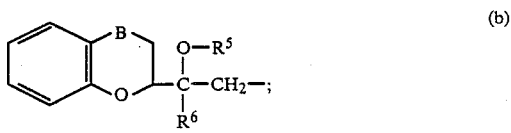

$R^5$ being hydrogen or $C_{1-12}$ alkylcarbonyl;
$R^6$ being hydrogen or $C_{1-6}$ alkyl;
$R^7$ being aryl, a radical $R^8$-O or a radical $R^8$-S;
B being a bivalent radical of formula $-CH_2-$ or $-O-$; and
said $R^8$ being hydrogen; aryl; 2,3-dihydro-1H-indenyl; benzodioxolyl; (2,3-dihydro-1,4-benzodioxin-2-yl)methyl; (2H-1-benzopyran-2-yl)methyl; or phenyl substituted with $C_{2-6}$ alkenyloxy, $C_{1-6}$ alkylcarbonylamino or $C_{1-6}$alkylphenylcarbonyl; and
wherein said substituted $C_{3-6}$ cycloalkyl is $C_{3-6}$ cycloalkyl being substituted with up to two substituents each independently selected from the group consisting of aryl, aryloxy and cyano;
said substituted $C_{1-6}$ alkyl is $C_{1-6}$ alkyl being substituted with a member selected from the group consisting of $C_{3-6}$ cycloalkyl, pyridinyl, pyridinyloxy, aryl, benzimidazolyl, indolyl, isoxazolyl being optionally substituted with phenyl, 3-oxo-1,2,4-triazolo[4,5-a]pyridin-2(3H)-yl, a radical of formula ArY—, a radical of formula $R^9O-$ and a radical of formula

said Ar being aryl;
Y being O, S, NH, —CONH—, —CHCN, —CHOR$^{10}$ or —SO$_2$;
$R^9$ being hydrogen, aryl $C_{1-6}$ alkyl, $C_{3-6}$ cycloalkyl, phenyl substituted with phenyl, or phenyl substituted with $C_{1-6}$ alkyloxycarbonyl;
$R^{10}$ being hydrogen or $C_{1-6}$ alkyl; and
wherein aryl is phenyl optionally substituted with up to three substituents each independently selected from the group consisting of $C_{1-6}$ alkyl, $C_{1-6}$ alkyloxy, halo, trifluoromethyl, cyano, $C_{1-6}$ alkylcarbonyl, nitro, amino and aminocarbonyl.

As used herein the term halo is generic to fluoro, chloro, bromo and iodo; "$C_{1-6}$ alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; $C_{1-12}$ alkyl is meant to include straight and branched saturated hydrocarbon radicals, having from 1 to 12 carbon atoms; "$C_{2-6}$ alkenyl" refers to alkenyl radicals having from 2 to 6 carbon atoms, such as, for example, 2-propenyl, 2-butenyl, 3-butenyl, 2-pentenyl and the like; and "$C_{3-6}$ cycloalkyl" embraces cyclopropyl, cyclobutyl, cyclopentyl and cyclohexyl.

Preferred compounds within the invention are those wherein L is aryl $C_{2-6}$ alkenyl, $C_{1-6}$ alkyl being substituted with aryloxy, a radical of formula (a) or a radical of formula (b).

Particularly preferred compounds within the invention are those wherein L is as described hereinabove for the preferred compounds and $-A^1=A^2-A^3=A^4-$ is $-CH=CH-CH=CH-$, n is the integer 1, $R^2$ is absent and a double bond exists between the nitrogen bearing $R^2$ and the interjacent carbon atom, and $R^3$ and $R^4$ are both hydrogen atoms.

More particularly preferred compounds within the invention are those wherein $-A^1=A^2-A^3=A^4-$, n, $R^2$ and $R^3$ are as defined hereinabove for the particularly preferred compounds and wherein a double bond exists between the nitrogen bearing $R^2$ and the interjacent carbon atom, and wherein L is $C_{1-6}$ alkyl substituted with aryloxy, a radical of formula (a) wherein $R^5$ and $R^6$ are both hydrogen and $R^7$ is a radical $R^8-O-$, wherein $R^8$ is aryl, or L is a radical of formula (b), wherein B is O, $R^5$ and $R^6$ are both hydrogen radicals.

Especially preferred compounds within the invention are those particularly preferred compounds wherein $R^1$ is $C_{1-6}$ alkyl and aryl is halophenyl.

The most preferred compounds are selected from the group consisting of 4-[(2-benzothiazolyl)methylamino]-α-[(4-fluorophenoxy)methyl]-1-piperidineethanol and the pharmaceutically acceptable acid addition salts thereof.

In order to simplify the structural representations of the compounds of formula (I) and of certain precursors and intermediates thereof the

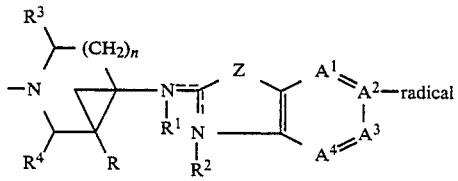

will hereafter be represented by the symbol D.

The compounds of formula (I) can generally be prepared by N-alkylating an intermediate of formula (III) with a reagent of formula (II).

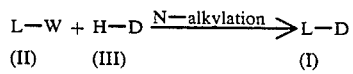

in (II) W represents an appropriate reactive leaving group such as, for example, halo, e.g., chloro, bromo or iodo, or a sulfonyloxy group, e.g. methylsulfonyl or 4-(methylphenyl)sulfonyloxy. The alkylation reaction is conveniently conducted in an inert organic solvent such as, for example, an aromatic hydrocarbon, e.g., benzene, methylbenzene, dimethylbenzene, and the like; a $C_{1-6}$ alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); dimethyl sulfoxide (DMSO); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The compounds of formula (I) can also be prepared by the reductive N-alkylation reaction of (III) with an appropriate carbonyl-compound of formula $L'=C=O$ (IV), said $L'=C=O$ being a compound of formula $L-H$ wherein a $-CH_2-$ radical is oxidized to a carbonyl radical.

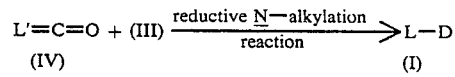

Said reductive N-alkylation reaction may conveniently be carried out by catalytically hydrogenating a stirred and heated mixture of the reactants in a suitable reaction-inert organic solvent according to art-known catalytic hydrogenating procedures. The reaction mixture may be stirred and/or heated in order to enhance the reaction rate. Suitable solvents are, for example, water; $C_{1-6}$ alkanols, e.g. methanol, ethanol, 2-propanol and the like; cyclic ethers, e.g. 1,4-dioxane and the like; halogenated hydrocarbons, e.g. trichloromethane and the like; N,N-dimethylformamide; dimethyl sulfoxide and the like; or a mixture of 2 or more of such solvents. The term "art-known catalytic hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I) can also be prepared by oxidatively cyclizing an urea or thiourea derivative of formula (V) in the presence of an appropriate oxidant.

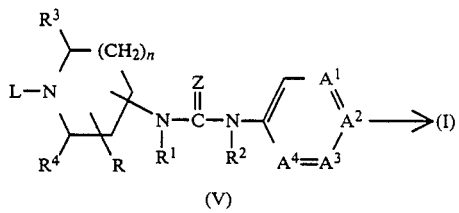

Appropriate oxidants are, for example, halogens, e.g. chlorine and bromine, thionyl chloride, sulfuryl chloride, thionyl bromide, sulfuryl bromide and the like agents. The said cyclization reaction is most conveniently conducted in a reaction-inert solvent such as, for example, an halogenated hydrocarbon, e.g. tetrachloromethane, trichloromethane and the like. Elevated temperatures may be appropriate to enhance the reaction rate.

The compounds of formula (I) wherein L is a radical of formula (a) or (b) wherein $R^5$ is hydrogen can also be prepared by reacting an appropriate oxirane derivative of formula (VI), respectively of formula (VIII) with (III). The thus obtained compounds of formula (I-a-1) respectively of formula (I-a-3) may further be converted into the corresponding compounds of formula (I-a-2), respectively (I-a-4) by an appropriate acylation reaction.

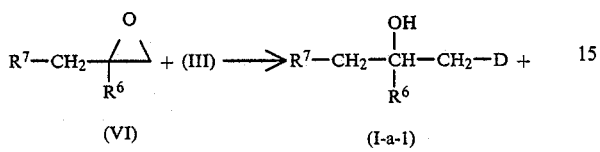

(VI)        (I-a-1)

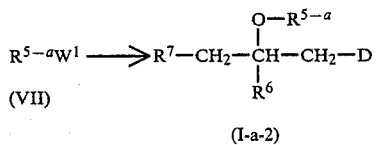

(VII)

(I-a-2)

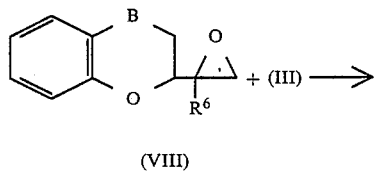

(VIII)

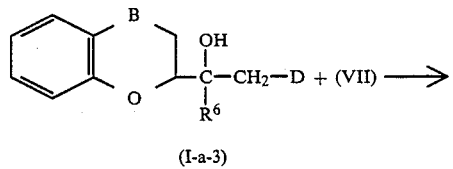

(I-a-3)

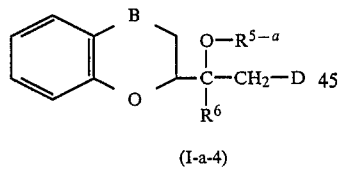

(I-a-4)

The reagent $R^{5-a}W^1$ represents an alkanoic acid or a reactive derivative thereof such as, for example, an ester, an acid halide or anhydride and the like.

The reaction of (VI) or (VIII) with (III) may conveniently be conducted in an appropriate solvent such as, for example, an aromatic hydrocarbon, e.g. benzene, methylbenzene and the like, a $C_{1-6}$ alkanol, e.g. methanol and ethanol. Elevated temperatures may be appropriate to enhance the reaction rate.

The compounds of formula (I), wherein $R^2$ is absent and a double bond exists between the nitrogen bearing $R^2$ and the previously defined interjacent carbon atom, said compounds being represented by the formula (I-b) can also be prepared by reacting an appropriate reagent of formula (IX) with a benzothiazole or benzoxazole of formula (X).

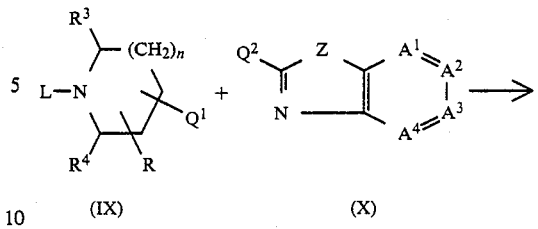

(IX)        (X)

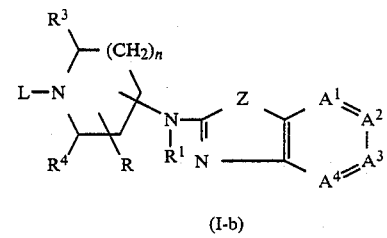

(I-b)

In (IX) and (X) $Q^1$ and $Q^2$ are selected so that during the alkylation reaction a radical of formula $-NR^1-$ is formed. For example, where $Q^1$ is an appropriate leaving group, $Q^2$ is a radical of formula $-NHR^1$, or where $Q^1$ is a radical of formula $-NHR^1$, $Q^2$ is an appropriate leaving group.

The compounds of formula (I-b) wherein Z is O and $R^1$ is hydrogen, said compounds being represented by the formula (I-b-1), can also be prepared by cyclodesulfurizing an intermediate of formula (XIV), which may conveniently be formed in situ by condensing an isothiocyanate (XII) with an aromatic aminoalcohol of formula (XIII).

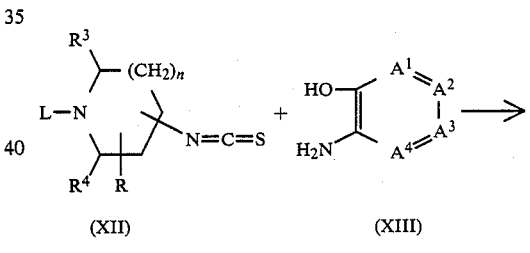

(XII)        (XIII)

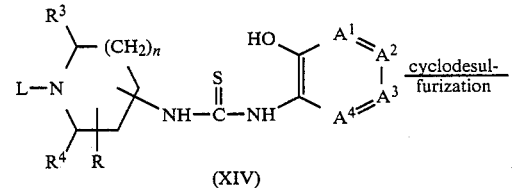

(XIV)

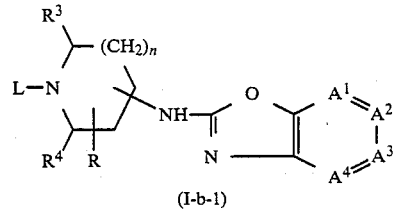

(I-b-1)

Said cyclodesulfurization reaction may be carried out by the reaction of (XIV) with an appropriate alkyl halide, preferably iodomethane in an appropriate reaction-inert organic solvent, e.g., a $C_{1-6}$ alkanol such as methanol, ethanol, 2-propanol and the like. Otherwise, the cyclodesulfurization reaction may be carried out by the reaction of (XIV) with an appropriate metal oxide or salt in an appropriate solvent according to art-known procedures. For example, the compounds of formula (I) can easily be prepared by the reaction of (XIV) with an appropriate Hg(II) or Pb(II) oxide or salt, such as, for example HgO, HgCl$_2$, Hg(OAc)$_2$, PbO or Pb(OAc)$_2$. In certain instances it may be appropriate to supplement the reaction mixture with a small amount of sulfur. Even so methanediimines, especially N,N'-methanetetraylbis[cyclohexanamine] may be used as cyclodesulfurizing agents.

The compounds of formula (I-b) wheren R$^1$ is hydrogen, said compounds being represented by the formula (I-b-2), may be prepared by cyclizing an intermediate (XVII), which in situ may be formed by reacting an isocyanate or isothiocyanate (XV) with an aromatic amine (XVI).

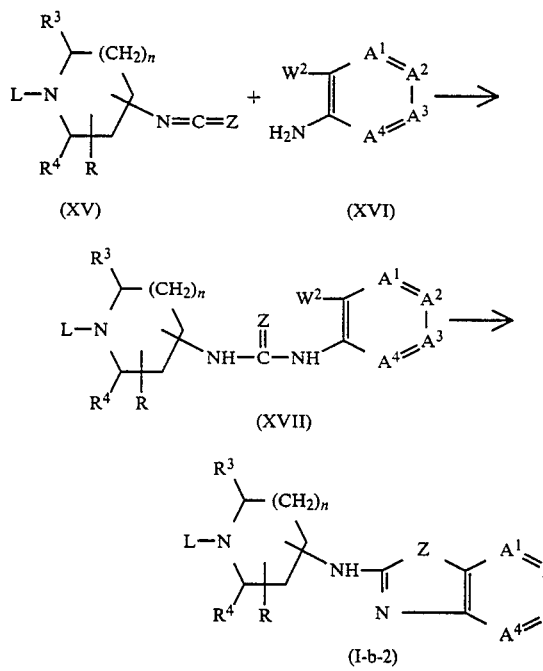

In (XVI) and (XVII) W$^2$ represents an appropriate leaving group such as, for example, halo, e.g. chloro and bromo; C$_{1-6}$ alkyloxy and C$_{1-6}$ alkylthio.

The compounds of formula (I) wherein L is a C$_{1-12}$ alkyl radical or a substituted C$_{1-6}$ alkyl radical, wherein said C$_{1-12}$ alkyl or C$_{1-6}$ alkyl contains at least two carbon atoms, said compounds being represented by the formula (I-c), may also be prepared by reacting an alkene of formula (XVIII) with an intermediate of formula (III) by stirring and, if desired, heating the reactants together, preferably in a suitable solvent such as, for example, an alcohol, e.g. methanol, ethanol, butanol and the like.

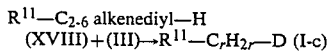
(XVIII)+(III)→R$^{11}$—C$_r$H$_{2r}$—D (I-c)

In (XVIII) R$^{11}$ represents C$_{1-6}$ alkyl, C$_{3-6}$ cycloalkyl, pyridinyl, pyridinyloxy, aryl, benzimidazolyl, indolyl, isoxazolyl being substituted with phenyl, 3-oxo-1,2,4-triazolo[4,5-a]pyridin-2(3H)-yl, a radical of formula ArY, a radical of formula R$^9$O and a radical of formula (g); and in (I-c) r is an integer of from 2 to 6 included.

Additionally, the compounds of formula (I), wherein L is a radical of formula Ar—CO—NH—CH$_2$—CH$_2$—, said compounds being represented by the formula (I-d), can also be prepared by reacting an aziridine of formula (XIX) with (III), preferably in the presence of a suitable solvent such as, for example, an aromatic hydrocarbon, e.g. benzene, methylbenzene and the like.

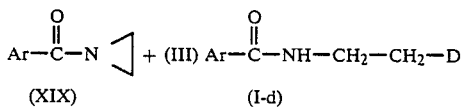

The compounds of formula (I) can also be converted into each other following art-known procedures. The compounds of formula (I) wherein R$^1$ is hydrogen may be converted into compounds of formula (I) wherein R$^1$ is other than hydrogen by reacting the former compounds with an appropriate N-alkylating reagent.

The compounds of formula (I) wherein L is a C$_{1-6}$ alkyl radical substituted with hydroxy may further be O-alkylated with an appropriate reagent following art-known O-alkylating procedures.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, benzoic, 2-hydroxybenzoic, 3-phenyl-2-propenoic, α-hydroxybenzeneacetic, 4-amino-2-hydroxybenzoic and the like acids. Conversely the salt form can be converted by treatment with alkali into the free base form.

A number of intermediates and starting materials in the foregoing preparations are known compounds which may be prepared according to art-known methodologies of preparing said or similar compounds. A number of such preparation methods will be described hereinafter in more detail.

The intermediates of formula (II) wherein L is C$_{1-6}$ alkyl being substituted with pyridinyloxy, aryloxy, arylthio, arylamino or a radical R$^{9-a}$O—, said R$^{9-a}$ having the previously defined meaning of R$^9$, provided that R$^{9-a}$ is other than hydrogen, can be prepared by alkylating an appropriate alcohol, thioalcohol or amine with a reagent W—C$_{1-6}$ alkyl-W, or alternatively with a reagent W-Alk-OH, and subsequently converting the thus formed alcohol with a reagent capable of converting an alcohol function into a reactive leaving group, e.g. thionyl chloride, methylsulfonyl chloride and the like.

The intermediates of formula (III) can generally be prepared by oxidatively cyclizing an urea or thiourea derivative of formula (XX), wherein P is an appropriate leaving group such as, for example, C$_{1-6}$ alkyloxycarbonyl, phenylmethoxycarbonyl, phenylmethyl and the like, following the same procedures described hereinabove for the preparation of (I) starting from (V) and, subsequently eliminating the protective group P in the thus obtained intermediate (XXI)

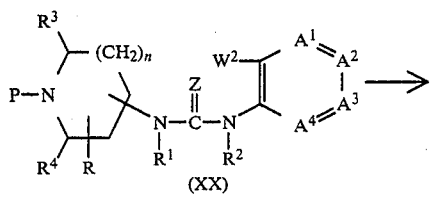
(XX)

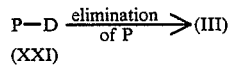

The elimination of the protective group P in (XXI) may generally be carried out following art-known procedures such as, for example, by hydrolysis in alkaline or acidic aqueous medium.

The intermediates of formula (III) wherein $R^2$ is absent and a double bond exists between the nitrogen bearing said $R^2$ and the previously defined interjacent carbon atom, and wherein Z is O, said intermediates being represented by the formula (III-a) may alternatively be prepared by cyclodesulfurizing a thiourea of formula (XXIII), which may in situ be formed by condensing an isothiocyanate of formula (XXII) with an aromatic alcohol (XIII) following the procedures described hereinabove for the preparation of (I-b-1) starting from (XII) and (XIII), and subsequently eliminating the protective group P in the thus obtained intermediate (XXIV) as described hereinabove.

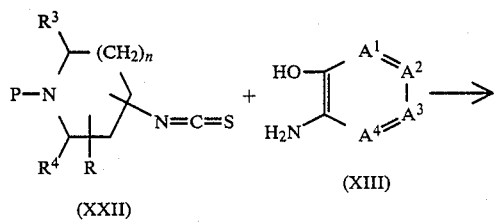

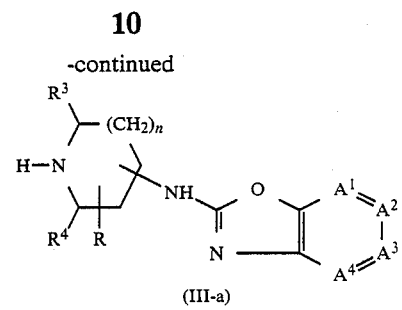
(III-a)

The intermediates of formula (III) wherein $R^2$ is absent and a double bond exists between the nitrogen bearing said $R^2$ and the previously defined interjacent carbon atom, said intermediates being represented by the formula (III-b) can also be prepared by cyclizing an intermediate (XXVI) which in situ may be formed by reacting an isocyanate or isothiocyanate (XXV) with (XVI), and subsequently eliminating the protective group P as described hereinabove.

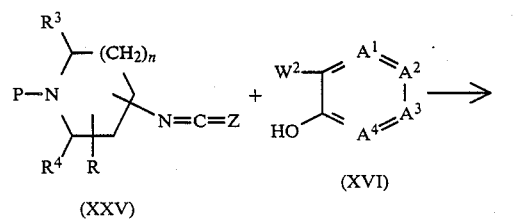

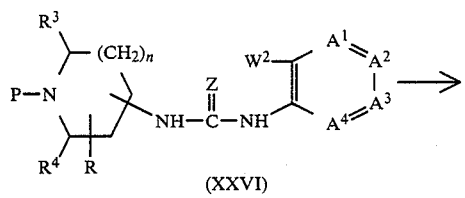

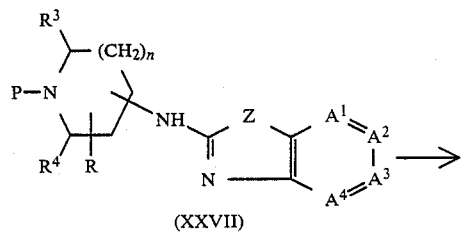

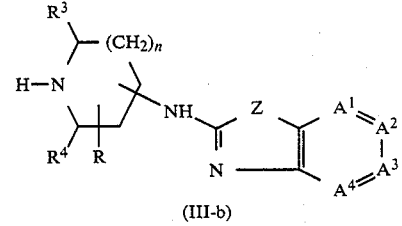
(III-b)

The previously described intermediates can also be converted into each other following art-known functional group transformation procedures.

For example, the intermediates of formula (V) wherein $R^1$ is hydrogen and the intermediates of formula (V) wherein $R^2$ is hydrogen, said intermediates being represented by the formula (V-a), respectively (V-b) can be prepared by reacting an isocyanate or isothiocyanate (XXVIII) with an aromatic amine (XXIX), respectively by reacting an amine (XXX) with an aromatic isocyanate or isothiocyanate (XXXI).

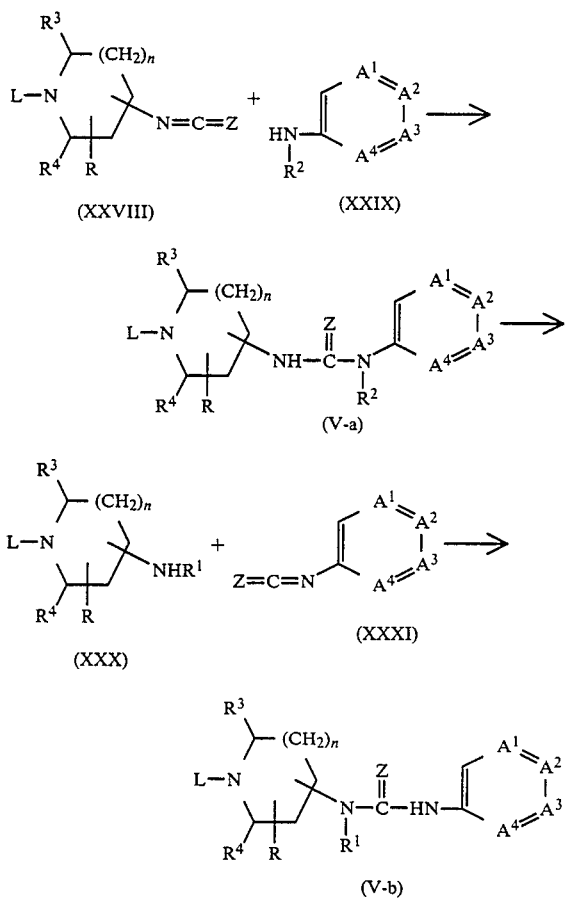

The intermediates of formula (VI) and of formula (VII) may be prepared by epoxidizing an alkene reagent of formula (XXXII) respectively of formula (XXXIII) with an appropriate epoxidizing reagent, e.g. with an aromatic peroxoacid, in a suitable solvent.

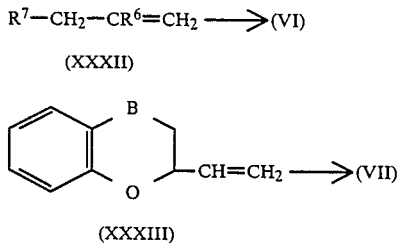

The intermediates of formula (XIX) may be prepared following the procedures described hereinabove for the preparation of (V-a) and (V-b).

During one of the reactions the intermediates wherein $R^1$ is hydrogen may be converted into the corresponding intermediates wherein $R^1$ is other than hydrogen following art-known N-alkylating procedures.

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The compounds of formula (I), their pharmaceutically acceptable acid-addition salts and stereochemically isomeric forms possess useful pharmacological properties. For example, they show useful anti-hypoxic and anti-anoxic properties, which activity is clearly evidenced by the experimental data obtained in e.g. the "KCN Test in Rats".

In view of their anti-anoxic or anti-hypoxic activity, the compounds of formula (I), their acid addition salts and/or their possible stereoisomers are very useful in the treatment of warm-blooded animals suffering from anoxia or hypoxia, for example, in such situations where the oxygen supply is reduced or blocked, such as shock, cardiac arrest, severe blood losses and the like situations.

In view of their anti-anoxic and anti-hypoxic activity the subject compounds may be formulated into various pharmaceutical forms for administration purposes. To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is also related with a method of treating hypoxia or anoxia in warm-blooded animals suffering from said hypoxia or anoxia by administering an effective anti-anoxic or hypoxic amount of a compound of formula (I) or a pharmaceutically acceptable acid addition salt thereof.

Although the amounts to be administered to subjects may vary within rather large limits, daily doses varying of from 0.1 mg/kg body weight to 40 mg/kg body weight are preferred.

The following examples are intended to illustrate and not to limit the scope of the present invention. Unless otherwise stated all parts therein are by weight.

EXPERIMENTAL PART

A. Preparation of Intermediates

EXAMPLE 1

A mixture of 100 parts of ethyl 4-oxo-1-piperidinecarboxylate, 42 parts of 2-propanamine, 2 parts of a solution of thiophene in methanol 4% and 400 parts of methanol was hydrogenated at normal pressure and at room temperature with 5 parts of palladium-on-charcoal catalyst 10%. After the calculated amount of hydrogen was taken up, the catalyst was filtered off and the filtrate was evaporated, yielding 118 parts (94%) of ethyl 4-[(1-methylethyl)amino]-1-piperidinecarboxylate (1).

In a similar manner there were also prepared:
ethyl 3-(methylamino)-8-azabicyclo[3,2,1]octane-8-carboxylate (2);
ethyl 3-(methylamino)-1-piperidinecarboxylate (3);
ethyl cis-3-(phenylmethoxy)-4-[(phenylmethyl)amino]-1-piperidinecarboxylate (4);
ethyl 4-(butylamino)-1-piperidinecarboxylate (5);
cis-ethyl 3-methoxy-4-(methylamino)-1-piperidinecarboxylate monohydrochloride; mp. 169.1° C. (6);
cis-ethyl 4-(methylamino)-3-(phenylmethoxy)-1-piperidinecarboxylate monohydrochloride; mp. 181.5° C. (7);
ethyl (cis+trans)-3-methyl-4-(methylamino)-1-piperidinecarboxylate (8); and
ethyl 3-(methylamino)-1-pyrrolidinecarboxylate (9).

EXAMPLE 2

A mixture of 150 parts of cis-ethyl 4-(methylamino)-3-(phenylmethoxy)-1-piperidinecarboxylate and 560 parts of methanol was hydrogenated at normal pressure and at 50° C. with 10 parts of palladium-on-charcoal catalyst 10%. After the calculated amount of hydrogen was taken up, the catalyst was filtered off and the filtrate was evaporated, yielding 101 parts (95%) of ethyl cis-3-hydroxy-4-(methylamino)-1-piperidinecarboxylate (10).

In a similar manner there was also prepared: cis-ethyl 4-amino-3-hydroxy-1-piperidinecarboxylate; bp. 175°-185° C. at 0.4 mm. pressure (11).

EXAMPLE 3

A mixture of 8.6 parts of sodium hydroxide and 120 parts of water was stirred at a temperature below 10° C. and there were added successively 17 parts of carbon disulfide and 35 parts of ethyl 3-amino-1-pyrrolidinecarboxylate. Stirring was continued for 3 hours. Then there were added dropwise 23.5 parts of ethyl carbonochloridate. Upon completion, stirring was continued for 2 hours at 60° C. The reaction mixture was extracted with methylbenzene. The extract was dried, filtered and evaporated, yielding 55 parts (100%) of ethyl 3-isothiocyanato-1-pyrrolidinecarboxylate (12).

In a similar manner there was also prepared: ethyl 4-isothiocyanato-1-piperidinecarboxylate (13).

EXAMPLE 4

A mixture of 107 parts of ethyl 4-isothiocyanato-1-piperidinecarboxylate, 53.5 parts of N-methylbenzenamine, 1 part of N,N-dimethyl-4-pyridinamine and 450 parts of methylbenzene was stirred and refluxed overnight. After cooling, the reaction mixture was evaporated. The residue was crystallized from 2,2'-oxybispropane. The product was filtered off and dried, yielding 68 parts (42%) of ethyl 4-[[(methylphenylamino)thioxomethyl]amino]-1-piperidinecarboxylate; mp. 95.2° C. (14).

In a similar manner there were also prepared:
ethyl 4-[(phenylamino)thioxomethylamino]-1-piperidinecarboxylate (15); and
ethyl 4-[[(2-hydroxyphenyl)aminothioxomethyl]amino]-1-piperidinecarboxylate; mp. 130° C. (16).

EXAMPLE 5

To a stirred solution of 91 parts of ethyl 4-(methylamino)-1-piperidinecarboxylate in 420 parts of 2,2'-oxybispropane were added dropwise 75 parts of 1-fluoro-3-isothiocyanatobenzene. Upon completion, stirring was continued for 1 hour. The precipitated product was filtered off and dried, yielding 150 parts (90%) of ethyl 4-[[(3-fluorophenyl)aminothioxomethyl]methylamino]-1-piperidinecarboxylate; mp. 175.2° C. (17).

In a similar manner there were also prepared:

$$CH_3-CH_2-O-\overset{O}{\underset{}{C}}-N\diagup\overset{R}{\underset{}{\diagdown}}\diagdown N-\overset{S}{\underset{R^1}{\underset{|}{C}}}-NH-\diagup\diagdown\text{base}\overset{R'}{}$$

| No. | $R^1$ | $R'$ | $R$ | isomerism | mp. (°C.) |
|---|---|---|---|---|---|
| 18 | H | H | OH | cis | 191.1 |
| 19 | $CH_3$ | H | H | — | 166.0 |
| 20 | $C_2H_5$ | H | H | — | oil |
| 21 | $n.C_4H_9$ | H | H | — | — |
| 22 | $CH_3$ | 4-$CH_3$ | H | — | — |
| 23 | $C_6H_5CH_2$ | H | H | — | — |
| 24 | $CH_3$ | 4-F | H | — | 178.6 |
| 25 | $CH_3$ | H | $OCH_3$ | cis | 166.0 |
| 26 | $CH_3$ | 3-OH | H | — | — |

-continued

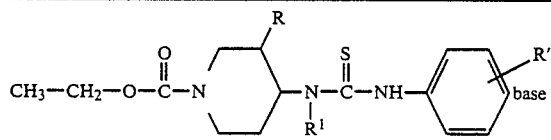

| No. | R¹ | R' | R | isomerism | mp. (°C.) |
|-----|-----|-----|-----|-----------|-----------|
| 27 | CH₃ | H | CH₃ | cis + trans | — |
| 28 | i.C₃H₇ | H | H | — | — |
| 29 | CH₃ | 3-CH₃O | H | — | — |
| 30 | CH₃ | 3-Cl | H | — | — |
| 31 | CH₃ | 4-OH | H | — | 200.0 |
| 32 | CH₃ | 4-Cl | H | — | 193.1 |
| 33 | CH₃ | 4-CH₃O | H | — | — |
| 34 | CH₃ | H | OH | cis | — |

In a similar manner there were also prepared:
ethyl 3-[methyl[(phenylamino)thioxomethyl]amino]-8-azabicyclo[3.2.1]octane-8-carboxylate; mp. 143.9° C. (35);
ethyl 3-[methyl[(phenylamino)thioxomethyl]amino]-1-piperidinecarboxylate (36); and
ethyl 3-[methyl[(phenylamino)thioxomethyl]amino]-1-pyrrolidinecarboxylate; mp. 145.4° C. (37).

EXAMPLE 6

A mixture of 55 parts of ethyl 3-isothiocyanato-1-pyrrolidinecarboxylate, 23.6 parts of 2-aminophenol and 320 parts of acetonitrile was stirred and refluxed for 4 hours. Then there were added 93 parts of mercury(II) oxide and 0.5 parts of sulfur while stirring vigorously. The reaction mixture was stirred and refluxed overnight. After cooling, the mixture was filtered over diatomaceous earth and the filtrate was evaporated. The residue was purified by column chromatography over silica gel using a mixture of trichloromethane and methanol (99:1 by volume) as eluent. The pure fractions were collected and the eluent was evaporated, yielding 38 parts (64%) of ethyl 3-[(2-benzoxazolyl)amino]-1-pyrrolidinecarboxylate as a residue (38).

In a similar manner there was also prepared:
ethyl 4-(2-benzoxazolylamino)-1-piperidinecarboxylate monohydrobromide (39).
ethyl 4-[(oxazolo[4,5-b]pyridin-2-yl)amino]-1-piperidinecarboxylate monohydrobromide; mp. 203.0° C. (40).

In a similar manner there is also prepared:
ethyl 4-[(oxazolo[4,5-d]pyridin-2-yl)amino]-1-piperidinercarboxylate (41).

EXAMPLE 7

To a stirred mixture of 196 parts of ethyl 4-[ethyl[(phenylamino)thioxomethyl]amino]-1-piperidinecarboxylate and 1600 parts of tetrachloromethane were added dropwise 89 parts of bromine at room temperature. Upon completion, stirring was continued first for 30 minutes at room temperature and further for 4 hours at reflux. The reaction mixture was cooled and the tetrachloromethane was decanted, yielding 194 parts (100%) of ethyl 4-[(2-benzothiazolyl)ethylamino]-1-piperidinecarboxylate as an oily residue (42).

In a similar manner there were also prepared:

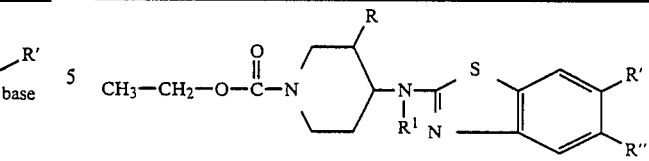

| No. | R¹ | R' | R | R'' | isomerism | salt/base | mp. (°C.) |
|-----|-----|-----|-----|-----|-----------|-----------|-----------|
| 43 | H | H | H | H | — | HBr | — |
| 44 | CH₃ | H | H | H | — | HBr | — |
| 45 | n.C₄H₉ | H | H | H | — | HBr | oil |
| 46 | CH₃ | CH₃ | H | H | — | base | — |
| 47 | C₆H₅CH₂ | H | H | H | — | base | — |
| 48 | CH₃ | H | OCH₃ | H | cis | base | — |
| 49 | CH₃ | H | H | F | — | base | oil |
| 50 | CH₃ | H | H | OH | — | HBr | — |
| 51 | CH₃ | H | CH₃ | H | cis + trans | HBr | — |
| 52 | i.C₃H₇ | H | H | H | — | HBr | — |
| 53 | CH₃ | H | H | OCH₃ | — | base | — |
| 54 | CH₃ | H | H | Cl | — | HBr | — |
| 55 | CH₃ | OH | H | H | — | HBr | — |
| 56 | CH₃ | Cl | H | H | — | HBr | — |
| 57 | CH₃ | H | OH | H | cis | base | — |
| 58 | H | H | OH | H | cis | base | — |

In a similar manner there were also prepared:
ethyl 3-[(2-benzothiazolyl)methylamino]-8-azabicyclo[3.2.1]octane-8-carboxylate (59);
ethyl 3-[(2-benzothiazolyl)methylamino]-1-piperidinecarboxylate (60);
ethyl 3-[(2-benzothiazolyl)methylamino]-1-pyrrolidinecarboxylate monohydrobromide (61); and
ethyl 4-[(3-methyl-2(3H)-benzothiazolyliden)amino]-1-piperidinecarboxylate (62).

EXAMPLE 8

To a stirred mixture of 103.1 parts of ethyl 4-[[[(3-chlorophenyl)amino]thioxomethyl]methylamino]-1-piperidinecarboxylate and 960 parts of tetrachloromethane were added dropwise 45.4 parts of bromine at about 20° C. Upon completion, stirring was continued first for 45 minutes at room temperature and further for 35 hours at reflux. The reaction mixture was cooled and the tetrachloromethane was decanted, yielding 126 parts (100%) of ethyl 4-[(7-chloro-2-benzothiazolyl)methylamino]-1-piperidinecarboxylate monohydrobromide as a residue (63).

EXAMPLE 9

To a stirred mixture of 124 parts of ethyl 4-[[[(4-methoxyphenyl)amino]thioxomethyl]methylamino]-1-piperidinecarboxylate and 1500 parts of tetrachloromethane were added dropwise slowly 112.6 parts of bromine at room temperature. Upon completion, stirring was continued first for 30 minutes at room temperature and then for 3 hours at reflux temperature. After cooling, tetrachloromethane was decanted, yielding 110 parts (73%) of ethyl 4-[(5-bromo-6-methoxy-2-benzothiazolyl)methylamino]-1-piperidinecarboxylate as a residue (64).

EXAMPLE 10

A mixture of 51 parts of ethyl 4-isothiocyanato-1-piperidinecarboxylate, 30 parts of 2-chloro-3-pyridinamine and 240 parts of ethanol was stirred and refluxed for 24 hours. The reaction mixture was cooled to room temperature. Upon the addition of 70 parts of 2,2'-oxybispropane, the product was allowed to crystallize.

It was filtered off and dried, yielding 40 parts (50%) of ethyl 4-(thiazolo[5,4-b]pyridin-2-ylamino)-1-piperidinecarboxylate monohydrochloride (65).

EXAMPLE 11

A mixture of 8.5 parts of ethyl 4-amino-1-piperidinecarboxylate and 2.6 parts of 2-(methylsulfonyl)thiazolo[4,5-c]pyridine was molten together for 1 hour at 120° C. After cooling, the mixture was taken up in trichloromethane. The whole was washed with water and sodium hydroxide, dried, filtered and evaporated. The residue was purified by column chromatography over silica gel using a mixture of trichloromethane and methanol (99:1 by volume) as eluent. The pure fractions were collected and the eluent was evaporated. The residue was stirred in warm 2,2'-oxybispropane. The product was filtered off and dried, yielding 2.8 parts (76%) of ethyl 4-[(thiazolo[4,5-c]pyridin-2-yl)amino]-1-piperidinecarboxylate; mp. 213° C. (66).

EXAMPLE 12

A mixture of 20 parts of ethyl 4-[(2-benzothiazolyl)-methylamino]-1-piperidinecarboxylate monohydrobromide and 300 parts of hydrobromic acid solution 48% in water was stirred and refluxed for 2 hours. The reaction mixture was evaporated and the residue was rystallized from methanol, yielding 17 parts (85%) of N-methyl-N-(4-piperidinyl)-2-benzothiazolamine dihydrobromide; mp. +260° C. (67).

A solution of 427 parts of N-methyl-N-(4-piperidinyl)-2-benzothiazolamine dihydrobromide monohydrate in 1500 parts of water was treated with a sodium hydroxide solution 50%. The product was extracted twice with trichloromethane. The combined organic layers were washed with water, dried, filtered and evaporated. The residue was crystallized from 490 parts of 2,2'-oxybispropane. The product was filtered off and dried, yielding 248 parts (100%) of N-methyl-N-(4-piperidinyl)-2-benzothiazolamine; mp. 86.9° C. (68).

In a similar manner there were also prepared:

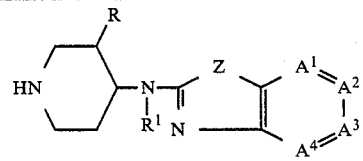

| No. | R | $R^1$ | $A^1=A^2-A^3=A^4$ | Z | isomerism | salt/base | mp. (°C.) |
|---|---|---|---|---|---|---|---|
| 69 | H | H | CH=CH—CH=CH | S | — | 2HBr | 260 |
| 70 | OH | H | CH=CH—CH=CH | S | cis | 2HBr.$H_2O$ | 268–300 |
| 71 | H | H | N=CH—CH=CH | S | — | 3HBr | 286.9 |
| 72 | H | $CH_3$ | N=CH—CH=CH | S | — | base | 144 |
| 73 | H | H | CH=CH—CH=CH | O | — | 2HBr | 263 |
| 74 | H | $CH_3$ | CH=CH—CH=CH | O | — | 2HBr.½$H_2O$ | 261.2 |
| 75 | H | $CH_3$ | CH=CH—CH=CH | O | — | base | 130.3 |
| 76 | H | $C_2H_5$ | CH=CH—CH=CH | S | — | * | 191.7 |
| 77 | H | n.$C_4H_9$ | CH=CH—CH=CH | S | — | ** | 160.0 |
| 78 | H | $CH_3$ | CH=C(CH_3)—CH=CH | S | — | base | 74.3 |
| 79 | H | $C_6H_5CH_2$ | CH=CH—CH=CH | S | — | * | 206.4 |
| 80 | $OCH_3$ | $CH_3$ | CH=CH—CH=CH | S | cis | $(COOH)_2$ | 206.4 |
| 81 | H | $CH_3$ | CH=CH—CF=CH | S | — | 2HCl.$H_2O$ | 266.4 |
| 82 | H | $CH_3$ | CH=CF—CH=CH | S | — | base | — |
| 83 | H | $CH_3$ | CH=CH—C(OH)=CH | S | — | 2HBr | — |
| 84 | H | i.$C_3H_7$ | CH=CH—CH=CH | S | — | * | 181 |
| 85 | H | $CH_3$ | CH=CH—C(OCH_3)=CH | S | — | base | — |
| 86 | H | $CH_3$ | CH=CH—C(Cl)=CH | S | — | * | 158 |
| 87 | H | $CH_3$ | C(Cl)=CH—CH=CH | S | — | base | — |
| 88 | H | $CH_3$ | CH=C(OH)—CH=CH | S | — | 2HBr | — |
| 89 | H | $CH_3$ | CH=C(Cl)—CH=CH | S | — | 2HCl.$H_2O$ | 237.8 |

-continued

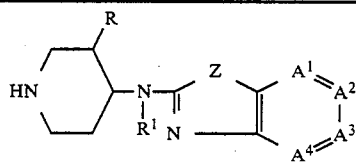

| No. | R | R¹ | A¹=A²—A³=A⁴ | Z | isomerism | salt/base | mp. (°C.) |
|---|---|---|---|---|---|---|---|
| 90 | H | $CH_3$ | CH=C—CBr=CH<br>\|<br>$OCH_3$ | S | — | base | 137.0 |
| 91 | OH | $CH_3$ | CH=CH—CH=CH | S | cis | base | — |

*: (Z)—2-butenedioate (1:1)
*: (Z)—2-butenedioate (2:3)

In a similar manner there were also prepared:
N-(1-methylthiazolo[5,4-b]pyridin-2(1H)-ylidene)-4-piperidinamine (92);
N-(2-benzothiazolyl)-N-methyl-8-azabicyclo[3.2.1]octan-3-amine (E)-2-butenedioate (1:1); mp. 236.1° C. (93);
N-methyl-N-(3-piperidinyl)-2-benzothiazolamine (94);
N-methyl-N-(3-pyrrolidinyl)-2-benzothiazolamine ethanedioate(1:1); mp. 157.0° C. (95);
N-(3-methyl-2(3H)-benzothiazolylidene-4-piperidinamine; mp. 198.5° C. (96);
N-methyl-N-(3-pyrrolidinyl)-2-benzoxazolamine (97);
N-(4-piperidinyl)thiazolo[4,5-c]pyridin-2-amine (98); and
N-(4-piperidinyl)oxoazolo[4,5-b]pyridin-2-amine (99).

In a similar manner there is also prepared:
N-(4-piperidinyl)oxoazolo[4,5-d]pyridin-2-amine (100).

EXAMPLE 13

A mixture of 100 parts of ethyl (cis+trans)-4-[(2-benzothiazolyl)methylamino]-3-methyl-1-piperidinecarboxylate monohydrobromide and 600 parts of a hydrobromic acid solution 48% in water was stirred and refluxed for 3 hours. After cooling, the reaction mixture was evaporated. The residue was crystallized from 2-propanol: two fractions were obtained. The first fraction was taken up in water. The solution was treated with sodium hydroxide. The product was extracted with trichloromethane. The organic layer was washed with water, dried, filtered and evaporated, yielding 30 parts (48%) of (cis+trans)-N-methyl-N-(3-methyl-4-piperidinyl)-2-benzothiazolamine (101) as an oily residue. The second fraction was taken up in water. The solution was treated with sodium hydroxide. The product was extracted with trichloromethane. The organic layer was washed with water, dried, filtered and evaporated. The residue was converted into the hydrobromide salt in methanol. The salt was filtered off and dried, yielding 16.6 parts (16%) of cis-N-methyl-N-(3-methyl-4-piperidinyl)-2-benzothiazolamine dihydrobromide; mp. 266.7° C. (102).

EXAMPLE 14

To a stirred mixture of 38 parts of ethyl 3-[(2-benzoxazolyl)amino]-1-pyrrolidinecarboxylate, 150 parts of dimethyl sulfoxide and 135 parts of benzene were added portionwise 7.25 parts of a sodium hydride dispersion 50% at a temperature below 10° C. After stirring for a while, 21.6 parts of iodomethane were added dropwise at the same temperature. Upon completion, stirring was continued overnight at 50° C. 1000 Parts of water were added and the product was extracted with methylbenzene. The extract was washed with water, dried, filtered and evaporated. The residue was converted into the hydrochloride salt in 2-propanol. The salt was filtered off and dried, yielding 40 parts (80%) of ethyl 3-[(2-benzoxazolyl)methylamino]-1-pyrrolidinecarboxylate dihyrochloride (103).

In a similar manner there were also prepared:
ethyl 4-[(2-benzoxazolyl)methylamino]-1-piperidinecarboxylate monohydrobromide; mp. 152.6° C. (104);
ethyl 4-(1-methylthiazolo[5,4-b]pyridin-2(1H)-ylidenamino)-1-piperidinecarboxylate (105); and
ethyl 4-[methyl(thiazolo[5,4-b)pyridin-2-yl)amino]-1-piperidinecarboxylate (106).

EXAMPLE 15

To a stirred mixture of 32.1 parts of 3-fluorophenol, 122 parts of 1,6-dibromohexane and 200 parts of water was dropwise added a solution of 20 parts of sodium hydroxide in 100 parts of water at reflux temperature. Upon completion, stirring was continued for 24 hours at reflux. After cooling, the product was extracted three times with trichloromethane. The combined extracts were dried, filtered and evaporated. The residue was distilled, yielding 40 parts (50%) of 1-[(6-bromohexyl)oxy]-3-fluorobenzene; bp. 45°–90° C. at 0.05 mm pressure (107).

In a similar manner there were also prepared:

| | Ar—Y—$(CH_2)_n$—W | | | | |
|---|---|---|---|---|---|
| No. | Ar | Y | n | W | physical data |
| 108 | 4-$C_6H_5$—$C_6H_4$ | O | 3 | Cl | mp. 61.5–63° C. |
| 109 | 2-$CH_3CO$, 4F—$C_6H_3$ | O | 3 | Cl | bp. 130–147° C. (0.2 mm Hg) |
| 110 | 4-$CH_3OCO$—$C_6H_4$ | O | 4 | Cl | bp. 157° C. (0.4 mm Hg) |
| 111 | 2F—$C_6H_4$ | O | 5 | Br | bp. 110–112° C. (0.6 mm Hg) |
| 112 | 4-$C_2H_5$—$C_6H_4$ | O | 5 | Br | bp. 128–134° C. (0.2 mm Hg) |
| 113 | 3-$CH_3O$—$C_6H_4$ | O | 5 | Br | bp. 150–154° C. (0.4 mm Hg) |
| 114 | 1-naphthalenyl | O | 5 | Br | bp. 165–170° C. (0.6 mm Hg) |
| 115 | 3-Cl—$C_6H_4$ | O | 5 | Br | bp. 135–137° C. (0.7 mm Hg) |

-continued

| No. | Ar | Y | n | W | physical data |
|---|---|---|---|---|---|
| 116 | 3-CH$_3$CO—C$_6$H$_4$ | O | 3 | Cl | bp. 120° C. (0.5 mm Hg) |
| 117 | 3,4,5(Cl)$_3$—C$_6$H$_2$ | O | 3 | Br | — |
| 118 | 2-NH$_2$CO, 4F—C$_6$H$_2$ | O | 3 | Cl | mp. 108° C. |
| 119 | 4-F—C$_6$H$_4$ | S | 3 | Br | bp. 78–80° C. (0.2 mm Hg) |
| 120 | 2,6-(Br)$_2$, 4CH$_3$—C$_6$H$_2$ | O | 3 | Br | bp. 118–123 (0.3 mm Hg) |
| 121 | 1-Br—2-naphthalenyl | O | 3 | Br | — |
| 122 | 3-F—C$_6$H$_4$ | O | 5 | Br | bp. 120° C. (0.1–0.30 mm Hg) |
| 123 | 3-F—C$_6$H$_4$ | O | 4 | Br | — |
| 124 | 4-CH$_3$CO—C$_6$H$_4$ | O | 5 | Br | bp. 165–170° C. (0.02 mm Hg) |

And following the same procedure and using the appropriate starting materials there were also prepared: [(6-bromo-2-naphthalenyloxy)methyl]oxirane (125); (4-methylphenyl)[4-(oxiranylmethoxy)phenyl]methanone (126); [(2,6-dimethylphenoxy)methyl]oxirane; bp. 85°–90° C. at 0.2 mm pressure (127); and [(2-bromo-4-fluorophenoxy)methyl]oxirane; bp. 105° C. at 66.5 Pa (128).

EXAMPLE 16

To a stirred and cooled (temp.≦0° C.) solution of 63 parts of 2-phenylcyclopropanemethanol in 378 parts of 1,1'-oxybisethane were added dropwise 63 parts of phosphor tribromide. The mixture was allowed to reach room temperature while stirring and the whole was further stirred for 30 minutes at room temperature. The reaction mixture was poured onto 90 parts of ice water and the layers were separated. The organic layer was washed successively twice with water and once with a sodium hydrogen carbonate solution, dried, filtered and evaporated. The residue was distilled, yielding 67 parts (74.5%) of (1-bromo-3-butenyl)benzene; bp. 85°–94° C. at 0.4 mm. pressure (129).

EXAMPLE 17

A ballon was charged with 32 parts of 1-[(3-chloropropyl)thio]-4-fluorobenzene, 50 parts of hydrogen peroxide and 112.5 parts of glacial acetic acid: exothermic reaction, the temperature rose to about 60° C. The whole was stirred and refluxed for one hour and further cooled while stirring for 3 hours. The cooled reaction mixture was then decomposed with 500 parts of water. The aqueous layer was separated and extracted once with 1,1'-oxybisethane. The combined organic layers were washed with water, dried over sodium sulfate and evaporated. The residue was recrystallized from 2,2'-oxybispropane, yielding, after cooling to −20° C., 18 parts of 1-[(3-chloropropyl)sulfonyl]-4-fluorobenzene (130).

EXAMPLE 18

To a stirred and refluxing mixture of 56 parts of lithium aluminum hydride in 1000 parts of tetrahydrofuran was added dropwise a solution of 359 parts of 2-(2,5-dimethylphenoxy)propanoic acid in 1000 parts of tetrahydrofuran. Upon completion, stirring was continued at reflux temperature for 1.50 hours. The reaction mixture was cooled and decomposed by the successive additions of 55 parts of water, 45 parts of a 15% sodium hydroxide solution and 190 parts of water and the whole was stirred for 30 minutes. The inorganic material was filtered off after acidification with hydrochloric acid solution. The filtrate was dried, filtered and evaporated. The residue was distilled, yielding 73 parts of 2-(2,5-dimethylphenoxy)-1-propanol; bp. 150° C. at 11 mm. pressure (131).

EXAMPLE 19

To a stirred and cooled mixture of 33.25 parts of 2-(phenylmethoxy)-1-propanol in 20 parts of pyridine was added dropwise a solution of 25.2 parts of methanesulfonyl chloride in 8 parts of pyridine at a temperature between 0° C. and 5° C. Upon completion, stirring was continued for 2 hours at room temperature. The reaction mixture was poured onto a mixture of crushed ice and ice water and the product was extracted three times with trichloromethane. The combined extracts were dried, filtered and evaporated. The oily residue was distilled, yielding 41 parts of 2-(phenylmethoxy)-1-propanol, methanesulfonate ester; bp. 151°–152° C. at 0.03 mm. pressure (132).

In a similar manner there were also prepared:
2-(3-methylphenoxy)-1-propanol, methanesulfonate ester; bp. 120° C. at 0.0002. pressure (133);
2-(2,6-dimethylphenoxy)-1-propanol, methanesulfonate ester; bp. 110° C. at 0.0002 mm. pressure (134);
2-(3,5-dimethylphenoxy)-1-propanol, methanesulfonate ester; bp. 115° C. at 0.0004 mm. pressure (135);
2-(2,6-dichlorophenyl)-1-propanol, methanesulfonate ester; bp. 120° C. at 0.002 mm. pressure (136);
3,4-dihydro-2H-1-benzopyran-2-methanol 4-methylbenzenesulfonate ester; mp. 59.4° C. (137).

EXAMPLE 20

A mixture of 6.72 parts of 4-fluorophenol, 8.4 parts of potassium carbonate and 200 parts of 4-methyl-2-pentanone was distilled azeotropically to dry. 17.1 Parts of 4-(phenylmethoxy)cyclohexyl methanesulfonate were added and the whole was stirred and refluxed over week-end using a water separator. After cooling, water was added and the layers were separated. The organic layer was washed with a sodium hydroxide solution and with water, dried, filtered and evaporated, yielding 17.7 parts (98.3%) of 1-fluoro-4-[[4-(phenylmethoxy)cyclohexyl]oxy]benzene as a residue (138).

A mixture of 17.1 parts of 1-fluoro-4-[[4-(phenylmethoxy)cyclohexyl]oxy]benzene and 160 parts of methanol was hydrogenated at normal pressure and at room temperature with 2 parts of palladium-on-charcoal catalyst 10%. After the calculated amount of hydrogen was taken up, the catalyst was filtered off over Hyflo and the filtrate was evaporated, yielding 8.9 parts (74.3%) of 4-(4-fluorophenoxy)cyclohexanol as a residue (139).

To a stirred and cooled mixture of 8.9 parts of 4-(4-fluorophenoxy)cyclohexanol and 160 parts of 2-propanone were added dropwise 13 parts of a solution of 26.7 parts of chromium trioxide in 42.3 parts of concentrate sulfuric acid diluted with water till a volume of 100 parts at a temperature below 5° C. Upon completion, stirring was continued for 3 hours at room temperature. After the addition of a few parts of methanol, the reaction mixture was poured onto water. The product was extracted with dichloromethane. The extract was dried, filtered and evaporated, yielding 8.4 parts (96.1%) of 4-(4-fluorophenoxy)cyclohexanone as a residue (140).

EXAMPLE 21

To a stirred and cooled (ice water bath) mixture of 72 parts of 2-ethenyl-3,4-dihydro-2H-1-benzopyran, 45 parts of sodium hydrogen carbonate and 2860 parts of dichloromethane were added quickly 102.4 parts of 3-chlorobenzenecarboperoxoic acid at about 10° C. The mixture was allowed to reach room temperature and stirring was continued for 4 days. The reaction mixture was filtered and the filtrate was washed successively with water, a saturate sodium sulfite solution, a 5% sodium hydroxide solution and again with water. The organic phase was dried, filtered and evaporated. The oily residue was purified by column chromatography over silica gel using a mixture of trichloromethane and petroleumether (50:50 by volume) as eluent.

The first fraction (unreacted starting material) was collected and the eluent was evaporated. The residue was taken up in 1300 parts of dichloromethane and 30 parts of 3-chlorobenzenecarboperoxoic acid were added at about 10° C. After stirring for 8 hours at room temperature another 30 parts of 3-chlorobenzenecarboperoxoic acid were added and stirring was continued for 12 hours. The mixture was filtered and the filtrate was washed successively with water, a saturate sodium sulfite solution, a 5% sodium hydroxide solution and again with water. The organic phase was dried, filtered and evaporated. The oily residue was purified by column chromatography over silica gel using a mixture of trichloromethane and petroleum-ether (50:50 by volume) as eluent. The pure fractions were collected and the eluent was evaporated, yielding 14 parts of crude product. The second fraction (A+B) was collected and the eluent was evaporated, yielding 28.0 parts of crude product. The combined crude fractions (resp. 14 and 28.0 parts) were separated by HPLC over silica gel using methylbenzene as eluent. The first fraction (A-isomer) was collected, yielding 12.5 parts of (A)-3,4-dihydro-2-oxiranyl-2H-1-benzopyran as a residue (141). The second fraction (B-isomer) was collected and the eluent was evaporated, yielding 14 parts of (B)-3,4-dihydro-2-oxiranyl-2H-1-benzopyran as a residue (142).

EXAMPLE 22

From a stirred mixture of 82 parts of a sodium methoxide solution 30% and 315 parts of N,N-dimethylformamide was distilled off 160 parts of the solvent (the temperature rose to 130° C.). After cooling to room temperature, there were added first 98 parts of trimethylsulfoxonium iodide and then 300 parts of dimethyl sulfoxide. The whole was stirred first for 30 minutes at room temperature and then for 1 hour at 50° C. The mixture was cooled to room temperature and 59 parts of 1-(4-fluorophenoxy)-2-propanone were added dropwise, during a period of 30 minutes. Upon completion, stirring was continued for 1 hour at room temperature and 2 hours at 50° C. After stirring overnight at room temperature, the reaction mixture was poured onto ice water. The product was extracted with 2,2'-oxybispropane. The organic layer was dried, filtered and evaporated, yielding 54 parts (84%) of 2-[(4-fluorophenoxy)methyl]-2-methyloxirane as a residue (143).

In a similar manner there was also prepared: (A−)-3,4-dihydro-2-oxiranyl-2H-1-benzopyran (144).

EXAMPLE 23

To a stirred solution of 2.7 parts of sodium in 50 parts of 2-methoxyethanol were added 13.2 parts of 4-fluorophenol. The whole was stirred for 15 minutes. A solution of 24.8 parts of (−)-(R)-2,2-dimethyl-1,3-dioxolane-4-methanol methanesulfonate (ester) in 70 parts of 2-methoxyethanol was added dropwise quickly. Stirring was continued for 1.5 hours at reflux temperature. After cooling, the mixture was poured into ice water. The product was extracted with methylbenzene. The extract was dried, filtered and evaporated, yielding 26 parts (97.3%) of (S)-4-[(4-fluorophenoxy)methyl]-2,2-dimethyl-1,3-dioxolane as a residue (145).

A mixture of 26 parts of (S)-4-[(4-fluorophenoxy)methyl]-2,2-dimethyl-1,3-dioxolane, 35 parts of a hydrochloric acid solution 2N and 80 parts of 2-propanone was stirred for 2 hours at reflux temperature. The mixture was stirred overnight at room temperature, diluted with 240 parts of ethanol and evaporated. The residue was dissolved in trichloromethane. The organic layer was washed twice with water, dried, filtered and evaporated. The residue was crystallized from tetrachloromethane. The product was filtered off and dried, yielding 11 parts (50.4%) of (−)-(R)-3-(4-fluorophenoxy)-1,2-propanediol; $[\alpha]_D = -10.08°$ (c=0.5% in methanol) (146).

To a stirred mixture of 11 parts of (−)-(R)-3-(4-fluorophenoxy)-1,2-propanediol, 23.3 parts of pyridine and 240 parts of trichloromethane were added 12.3 parts of 4-methylbenzenesulfonyl chloride. The whole was stirred overnight at room temperature. It was washed successively with acid water, a sodium carbonate solution and water, dried, filtered and evaporated. The residue was purified by column chromatography over silica gel using a mixture of trichloromethane and methanol (98:2 by volume) as eluent. The pure fractions were collected and the eluent was evaporated, yielding 13.5 parts (67.2%) of (+)-(S)-3-(4-fluorophenoxy)-1,2-propanediol, $O^1$-4-methylbenzenesulfonate; $[\alpha]_D = +11.11°$ (c=0.5% in trichloromethane) (147).

To a stirred mixture of 13.4 parts of (+)-(S)-3-(4-fluorophenoxy)-1,2-propanediol, $O^1$-4-methylbenzenesulfonate and 45 parts of tetrahydrofuran were added 4.9 parts of kalium 1,1-dimethyl ethoxide. The whole was stirred for 30 minutes at room temperature. It was filtered over Hyflo, washed with tetrahydrofuran and the filtrate was evaporated. The residue was distilled, yielding 3.8 parts (57.3%) of (−)-(R)-[(4-fluorophenoxy)methyl]oxirane; bp. 54° C. at 66.5 Pa; $[\alpha]_D = 4.08$ (c=0.5% in trichloromethane) (148).

In a similar manner there was also prepared: (+)-(S)-[(4-fluorophenoxy)methyl]oxirane; bp. 52°–53° C. at 66.5 Pa; $[\alpha]_D = +5.27$ (c=0.5% in methanol) $[\alpha]_D = +9.10$ (c=0.5% in dichloromethane) (149).

(B) Preparation of Final compounds

EXAMPLE 24

A mixture of 4.4 parts of 1-chloro-3-(4-chlorobutoxy)benzene, 3.7 parts of N-methyl-N-(4-piperidinyl)-2-benzothiazolamine, 2.1 parts of sodium carbonate and 90 parts of N,N-dimethylformamide was stirred for 24 hours at 60° C. The reaction mixture was cooled and poured onto water. The product was extracted with methylbenzene. The extract was washed with water, dried, filtered and evaporated. The residue was purified by column chromatography over silica gel using a mixture of trichloromethane and methanol (97:3 by volume) as eluent. The pure fractions were collected and the eluent was evaporated. The residue was converted into the (Z)-2-butenedioate salt in 2-propanone. The salt was filtered off and dried, yielding 4 parts (49%) of N-[1-[4-(3-chlorophenoxy)butyl]-4-piperidinyl]-N-methyl-2-benzothiazolamine (Z)-2-butenedioate (1:1); mp. 138.6° C. (1).

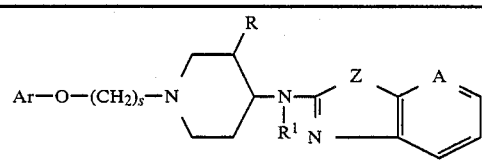

| No. | Ar | s | R | R¹ | Z | A | base salt | mp in °C. |
|---|---|---|---|---|---|---|---|---|
| 2 | $C_6H_5$ | 3 | H | H | O | CH | base | 123.2 |
| 3 | $C_6H_5$ | 3 | H | $CH_3$ | O | CH | base | 95.1 |
| 4 | $C_6H_5$ | 2 | H | $CH_3$ | O | CH | 1½$HNO_3$ | 126 |
| 5 | $C_6H_5$ | 2 | H | H | O | CH | base | 132 |
| 6 | 4-Cl—$C_6H_4$ | 3 | H | $CH_3$ | S | CH | base | 111.9 |
| 7 | $C_6H_5$ | 3 | H | $CH_3$ | S | CH | base | 97.6 |
| 8 | 4-Cl—$C_6H_4$ | 3 | H | $CH_3$ | O | CH | base | 87.5 |
| 9 | 3-F—$C_6H_4$ | 3 | H | $CH_3$ | S | CH | base | 92.6 |
| 10 | $C_6H_5$ | 4 | H | $CH_3$ | S | CH | * | 154.4 |
| 11 | 4-F—$C_6H_4$ | 4 | H | $CH_3$ | S | CH | base | 71.0 |
| 12 | 4-Cl—$C_6H_4$ | 4 | H | $CH_3$ | S | CH | * | 142.7 |
| 13 | $C_6H_5$ | 2 | H | $CH_3$ | S | CH | * | 174.5 |
| 14 | 4-$CH_3$—$C_6H_4$ | 3 | H | $CH_3$ | S | CH | base | 90.0 |
| 15 | 4-Cl—$C_6H_4$ | 4 | H | $CH_3$ | O | CH | base | 96.4 |
| 16 | 4-F—$C_6H_4$ | 4 | H | $CH_3$ | O | CH | base | 88.4 |
| 17 | 4-Cl—$C_6H_4$ | 2 | H | $CH_3$ | S | CH | base | 89.2 |
| 18 | 2-F—$C_6H_4$ | 3 | H | $CH_3$ | S | CH | base | 129.3 |
| 19 | 4-$CH_3O$—$C_6H_4$ | 3 | H | $CH_3$ | O | CH | base | 79.3 |
| 20 | 4-$CH_3$—$C_6H_4$ | 3 | H | $CH_3$ | O | CH | * | 200.2 |
| 21 | 4-i.$C_3H_7$—$C_6H_4$ | 3 | H | $CH_3$ | S | CH | * | 180.4 |
| 22 | 2,4-$(Cl)_2$—$C_6H_3$ | 3 | H | $CH_3$ | S | CH | * | 179.3 |
| 23 | 4-Br—$C_6H_4$ | 3 | H | $CH_3$ | S | CH | * | 167.2 |
| 24 | 4-$CH_3O$—$C_6H_4$ | 3 | H | $CH_3$ | S | CH | base | 146.5 |
| 25 | 1-naphthalenyl | 3 | H | $CH_3$ | S | CH | * | 154.9 |
| 26 | 4-$CH_3O$—$C_6H_4$ | 3 | H | $CH_3$ | S | CH | base | 156.0 |
| 27 | 4-$CH_3$—$C_6H_4$ | 2 | H | $CH_3$ | S | CH | * | 172.3 |
| 28 | 4-$CH_3$—$C_6H_4$ | 4 | H | $CH_3$ | S | CH | * | 155.5 |
| 29 | 4-Cl,2-$CH_3$—$C_6H_4$ | 3 | H | $CH_3$ | S | CH | base | 106.8 |
| 30 | 2-Cl—$C_6H_4$ | 3 | H | $CH_3$ | S | CH | base | 111.4 |
| 31 | 4-$CH_3O$—$C_6H_4$ | 4 | H | $CH_3$ | S | CH | base | 89.4 |
| 32 | 4-F—$C_6H_4$ | 5 | H | $CH_3$ | S | CH | * | 143.5 |
| 33 | 4-$C_6H_5$—$C_6H_4$ | 3 | H | $CH_3$ | S | CH | base | 126.6 |
| 34 | 2,6-$Cl_2$—$C_6H_3$ | 3 | H | $CH_3$ | S | CH | base | 116.9 |
| 35 | 3,4,5-$Cl_3$—$C_6H_2$ | 3 | H | $CH_3$ | S | CH | * | 181.3 |
| 36 | $C_6H_5$ | 6 | H | $CH_3$ | S | CH | ** | 127.6 |
| 37 | 2-$NH_2CO$,4-F—$C_6H_3$ | 3 | H | $CH_3$ | S | CH | base | 146.4 |
| 38 | $C_6H_5$ | 4 | H | $CH_3$ | O | CH | base | 71.8 |
| 39 | 2,6-$(CH_3)_2C_6H_3$ | 3 | H | $CH_3$ | S | CH | * | 175.6 |
| 40 | 3-$CH_3$—$C_6H_4$ | 3 | H | $CH_3$ | S | CH | base | 86.3 |
| 41 | 2-$CH_3$—$C_6H_4$ | 3 | H | $CH_3$ | S | CH | base | 93.2 |
| 42 | 4-Br—$C_6H_4$ | 4 | H | $CH_3$ | S | CH | ** | 120.5 |
| 43 | 4-$CH_3O$—$C_6H_4$ | 5 | H | $CH_3$ | S | CH | * | 150.7 |
| 44 | 2,4,5-$Br_3$—$C_6H_2$ | 3 | H | $CH_3$ | S | CH | * | 164.2 |
| 45 | 4-$CH_3$—$C_6H_4$ | 4 | H | $CH_3$ | O | CH | base | 85.4 |
| 46 | 2,4-$Cl_2$—$C_6H_4$ | 3 | H | $CH_3$ | O | CH | base | 100.9 |
| 47 | 4-$CH_3O$—$C_6H_4$ | 4 | H | $CH_3$ | O | CH | base | 69.5 |
| 48 | 3-$CH_3$—$C_6H_4$ | 3 | H | $CH_3$ | O | CH | base | 83.3 |
| 49 | 1-naphthalenyl | 5 | H | $CH_3$ | S | CH | * | 176.5 |
| 50 | 2-$CH_3O$—$C_6H_4$ | 5 | H | $CH_3$ | S | CH | base | 77.4 |
| 51 | 3-$CH_3CO$—$C_6H_4$ | 3 | H | $CH_3$ | S | CH | ** | 128.8 |
| 52 | 4-$CH_3CO$—$C_6H_4$ | 4 | H | $CH_3$ | S | CH | * | 144.3 |
| 53 | 2-Br,4-$CH_3$—$C_6H_3$ | 3 | H | $CH_3$ | S | CH | base | 116.3 |
| 54 | 1-Br—2-naphthalenyl | 3 | H | $CH_3$ | S | CH | * | 196.1 |
| 55 | $C_6H_5$ | 4 | H | H | S | CH | base | 115.3 |
| 56 | 4-$CH_3$—$C_6H_4$ | 3 | H | H | S | CH | base | 118.5 |
| 57 | 3-F—$C_6H_4$ | 3 | H | H | S | CH | base | 92.5 |
| 58 | 3-Cl—$C_6H_4$ | 4 | H | $CH_3$ | S | CH | base | 98.2 |
| 59 | 2-$CH_3$—$C_6H_4$ | 3 | H | $CH_3$ | O | CH | base | 90.1 |
| 60 | 4-Cl—$C_6H_4$ | 4 | H | $n.C_4H_9$ | S | CH | *** | 158.5 |
| 61 | 4-$CH_3O$—$C_6H_4$ | 4 | H | $n.C_4H_9$ | S | CH | *** | 136.4 |
| 62 | 4-Br—$C_6H_4$ | 4 | H | $CH_3$ | O | CH | base | 101.2 |
| 63 | 4-$CH_3$—$C_6H_4$ | 3 | H | $n.C_4H_9$ | S | CH | *** | 141.2 |
| 64 | $C_6H_5$ | 4 | H | $n.C_4H_9$ | S | CH | *** | 147.6 |
| 65 | 4-F—$C_6H_4$ | 4 | H | $n.C_4H_9$ | S | CH | *** | 144.0 |
| 66 | 3-F—$C_6H_4$ | 3 | H | $n.C_4H_9$ | S | CH | *** | 143.0 |

-continued

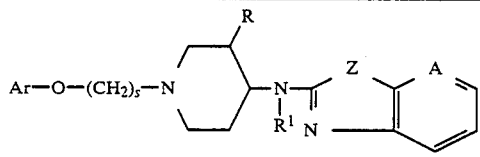

| No. | Ar | s | R | R¹ | Z | A | base salt | mp in °C. |
|---|---|---|---|---|---|---|---|---|
| 67 | 2-CH₃—C₆H₄ | 5 | H | CH₃ | S | CH | * | 157.3 |
| 68 | 4-t.C₄H₉ | 3 | H | CH₃ | S | CH | * | 197.0 |
| 69 | 4-Cl—C₆H₄ | 3 | H | CH₃ | S | CH | base | 111.8 |
| 70 | 4-CH₃CO—C₆H₄ | 5 | H | CH₃ | S | CH | H₂O | 91.6 |
| 71 | 3-CH₃O—C₆H₄ | 3 | H | CH₃ | S | CH | ** | 133.0 |
| 72 | 3-F—C₆H₄ | 3 | CH₃ | CH₃ | S | CH | base cis isomer | 104.4 |
| 73 | 3-CH₃—C₆H₄ | 3 | CH₃ | CH₃ | S | CH | base cis isomer | 79.5 |
| 74 | 4-CH₃O—C₆H₄ | 4 | CH₃ | CH₃ | S | CH | base cis isomer | 73.4 |
| 75 | C₆H₅ | 4 | CH₃ | CH₃ | S | CH | base cis isomer | 95.7 |
| 76 | 4-F—C₆H₄ | 4 | H | H | S | N | base | 146.5 |
| 77 | 3-F—C₆H₄ | 3 | H | H | S | N | base | 155.8 |
| 78 | C₆H₅ | 4 | H | H | S | N | base | 137.6 |
| 79 | 4-CH₃O—C₆H₄ | 4 | H | H | S | N | base | 104.2 |
| 80 | 3-Cl—C₆H₄ | 4 | H | H | S | N | base | 110.7 |
| 81 | 3-CH₃—C₆H₄ | 3 | H | H | S | N | base | 163.9 |
| 82 | C₆H₅ | 4 | H | CH₃ | S | N | * | 164.3 |
| 83 | 3-F—C₆H₄ | 3 | H | CH₃ | S | N | * | 144.9 |
| 84 | 3-Cl—C₆H₄ | 4 | H | CH₃ | S | N | * | 148.3 |

\*: (Z)—2-butenedioate (1:1)
\*\*: (Z)—2-butenedioate (1:2)
\*\*\*: (E)—2-butenedioate (1:1)

In a similar manner there were also prepared:

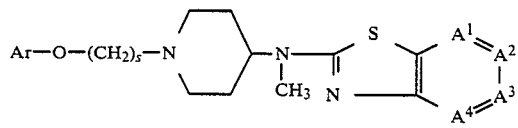

| No. | Ar | s | A¹=A²—A³=A⁴ | base/ salt | mp in °C. |
|---|---|---|---|---|---|
| 85 | 3-F—C₆H₄ | 3 | CH=CH—C(OH)=CH | base | 151.8 |
| 86 | 3-CH₃—C₆H₄ | 3 | CH=CH—C(OH)=CH | base | 135.5 |
| 87 | 3-F—C₆H₄ | 3 | CH=C(OH)—CH=CH | 2(COOH)₂ | 176.3 |
| 88 | 3-CH₃—C₆H₄ | 3 | CH=C(OH)—CH=CH | **** | 212.2 |
| 89 | 3-CH₃—C₆H₄ | 3 | CH=CCl—CH=CH | base | 89.8 |
| 90 | C₆H₅ | 4 | CH=CCl—CH=CH | base | 84.7 |
| 91 | 4-CH₃O—C₆H₄ | 4 | CH=CCl—CH=CH | base | 94.5 |
| 92 | 3-F—C₆H₄ | 3 | CH=CCl—CH=CH | base | 123.2 |

\*\*\*\*: (E)—2-butenedioate (2:1)

In a similar manner there were also prepared:

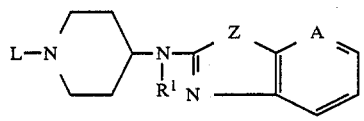

| No. | L | R¹ | Z | A | base salt | mp in °C. |
|---|---|---|---|---|---|---|
| 93 | n.butyl | H | S | N | base | 170.5 |
| 94 | (2,3-dihydro-1,4-benzodioxin-2-yl)CH₂— | H | S | N | base | 157.9 |
| 95 | n.butyl | H | O | CH | base | 139.2 |
| 96 | n.hexyl | H | S | N | base | 152 |
| 97 | n.butyl | CH₃ | S | N | HCl | 273.6 (dec.) |
| 98 | C₆H₅(CH₂)₂ | H | O | CH | base | 130.5 |
| 99 | (2,3-dihydro-1,4-benzodioxin-2-yl)CH₂— | H | O | CH | base | 144.6 |
| 100 | n.hexyl | CH₃ | O | CH | base | 54.8 |
| 101 | 4-CH₃O—C₆H₄—(CH₂)₂— | CH₃ | O | CH | base | 113.1 |
| 102 | C₆H₅CH=CH—CH₂ | CH₃ | O | CH | 2HBr | 247.2 |
| 103 | n.butyl | CH₃ | O | CH | 2HBr | 230.9 |
| 104 | (2,3-dihydro-1,4-benzodioxin-2-yl)CH₂— | CH₃ | O | CH | 2HBr | 192.8 |
| 105 | 4-CH₃O—C₆H₄—(CH₂)₂— | H | O | CH | base | 147.6 |
| 106 | n.hexyl | H | O | CH | 2HNO₃ | 141.5 |
| 107 | C₆H₅CH=CH—CH₂— | H | O | CH | base | 123.4 |
| 108 | C₆H₅—(CH₂)₅— | CH₃ | S | CH | * | 152.5 |
| 109 | n.undecyl | CH₃ | S | CH | * | 163.5 |
| 110 | C₆H₅CH₂O—(CH₂)₃— | CH₃ | S | CH | * | 135.2 |
| 111 | C₆H₅CH(OCH₃)— | CH₃ | S | CH | * | 150.3 |
| 112 | HO—(CH₂)₃— | CH₃ | S | CH | base | 89.2 |
| 113 | (4-F—C₆H₄)₂CHO—(CH₂)₂— | CH₃ | S | CH | (COOH)₂ | 171.1 |
| 114 | 4-F—C₆H₄—SO₂—(CH₂)₃— | CH₃ | S | CH | base | 130.4 |

*(Z)—2-butenedioate (1:1)

And following the same procedures and using the appropriate starting materials there were also prepared:

1-butyl-N-(1-methylthiazolo[5,4-b]pyridin-2(1H)-ylidene)-4-piperidinamine dihydrochloride.monohydrate; mp. 253.1° C. (115);

N-(1-methylthiazolo[5,4-b]pyridin-2(1H)-ylidene)-1-(2-phenylethyl)-4-piperidinamine dihydrochloride.-monohydrate; mp. 251.7° C. (116);

N-methyl-N-[1-(1-phenyl-3-butenyl)-4-piperidinyl]-2-benzothiazolamine (Z)-2-butenedioate (1:2) monohydrate; mp. 101.7° C. (117);

N-[1-[4-(4-fluorophenoxy)butyl]-3-pyrrolidinyl]-N-methyl-2-benzothiazolamine dihydrochloride.-monohydrate; mp. 152.5° C. (118);

N-[1-[4-(3-chlorophenoxy)butyl]-3-pyyrolidinyl]-N-methyl-2-benzothiazolamine ethanedioate(1:1); mp. 162.7° C. (119);

N-methyl-N-[1-[3-(3-methylphenoxy)propyl]-3-pyrrolidinyl]-2-benzothiazolamine ethanedioate(1:1); mp. 108.4° C. (120);

N-[1-[3-(3-fluorophenoxy)propyl]-3-pyrrolidinyl]-N-methyl-2-benzothiazolamine ethanedioate(1:1); mp. 137.0° C. (121); and N-methyl-N-[1-(4-phenoxybutyl)-3-pyrrolidinyl]-2-benzothiazolamine ethanedioate(1:1); mp. 150.2° C. (122).

EXAMPLE 25

A mixture of 5.04 parts of 1-(3-bromopropoxy)-4-methylbenzene, 7.54 parts of N-ethyl-N-(4-piperidinyl)-2-benzothiazolamine (Z)-2-butenedioate (1:1), 5.3 parts of sodium carbonate, 0.1 parts of potassium iodide and 180 parts of N,N-dimethylformamide was stirred and heated overnight at 60° C. The reaction mixture was poured onto water and the product was extracted with methylbenzene. The extract was washed three times with water, dried, filtered and evaporated. The residue was crystallized from 2-propanol, yielding 6 parts (75%) of N-ethyl-N-[1-[3-(4-methylphenoxy)propyl]-4-piperidinyl]-2-benzothiazolamine; mp. 101.0° C. (123).

Following the same procedures and, if desired, after converting the reaction product into the desired acid addition salt, there were also prepared:

-continued

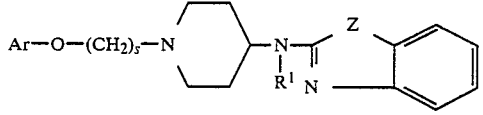

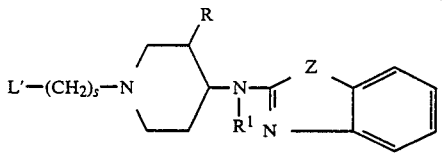

| No. | L' | s | R | R¹ | Z | base/salt | mp. in °C. |
|---|---|---|---|---|---|---|---|
| 124 | C₆H₅ | 2 | H | H | S | base | 118.1 |
| 125 | C₆H₅ | 2 | OH | H | S | base | 140.1 |
|  |  |  |  |  |  | (cis-isomer) |  |
| 126 | 2,3-dihydro-1,4-benzo-dioxine-2-yl | 1 | H | CH₃ | S | base | 123.6 |
| 127 | H | 4 | H | CH₃ | S | HCl | 232.6 |
| 128 | H | 4 | H | H | S | base | 116.8 |
| 129 | 2,3-dihydro-1,4-benzo-dioxin-2-yl- | 1 | H | H | S | base | 154.7 |
| 130 | 4-F—C₆H₄—S— | 3 | H | CH₃ | S | * | 158.0 |
| 131 | 4-F—C₆H₄—S— | 3 | H | CH₃ | O | base | 87.5 |
| 132 | 4-F—C₆H₄—S— | 3 | H | CH₃ | O | * | 173.4 |
| 133 | C₆H₅—CH=CH— | 1 | H | CH₃ | S | base | 101.3 |
| 134 | 1H-benzimidazol-1-yl- | 3 | H | CH₃ | S | ** | 168.7 |
| 135 | 4-F—C₆H₄—CH(CN)— | 3 | H | CH₃ | S | (COOH)₂ | 190.1 |
| 136 | HOCH₂—CH(OH)— | 1 | H | CH₃ | S | 2HCl.H₂O | 218.4 |
| 137 | C₆H₅—NH— | 2 | H | CH₃ | S | 3HCl.2H₂O | 204.7 |
| 138 | C₆H₅)₂CH—O— | 2 | H | CH₃ | S | (COOH)₂ ½H₂O | 190.4 |
| 139 | C₆H₅CH(CH₃)—O— | 2 | H | CH₃ | S | * | 165.0 |
| 140 | H | 10 | H | CH₃ | S | * | 165.3 |
| 141 | 5-phenyl-3-isoxazolyl | 2 | H | CH₃ | S | * | 183.0 |
| 142 | HO— | 2 | H | CH₃ | S | * | 175.0 |
| 143 | 4-F—C₆H₄CH—C₂H₅ | 1 | H | CH₃ | S | * | 180.5 |
| 144 | 4-F—C₆H₄CH(OH)— | 3 | H | CH₃ | S | ** | 145.5 |
| 145 | C₆H₅—CH=CH | 1 | H | C₂H₅ | S | (COOH)₂ | 199.6 |

In a similar manner there were also prepared:

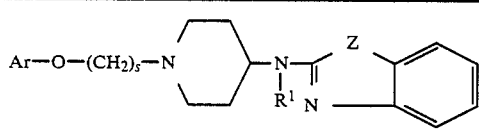

| No. | Ar | s | R¹ | Z | base/salt | mp. in °C. |
|---|---|---|---|---|---|---|
| 146 | 4-F—C₆H₄ | 3 | CH₃ | S | base | 97.7 |
| 147 | 4-F—C₆H₄ | 3 | CH₃ | O | base | 113.1 |
| 148 | 2-naphthalenyl | 3 | CH₃ | S | base | 113.7 |
| 149 | 2,6-Br₂, 4-CH₃C₆H₂ | 3 | CH₃ | S | * | 169.7 |
| 150 | 4-C₂H₅—C₆H₄ | 5 | CH₃ | S | * | 163.1 |
| 151 | 4-NO₂—C₆H₄ | 3 | CH₃ | S | base | 138.9 |
| 152 | 2-naphthalenyl | 5 | CH₃ | S | * | 193.9 |
| 153 | 3-CF₃—C₆H₄ | 3 | CH₃ | S | * | 149.4 |
| 154 | 3-CH₃O—C₆H₄ | 4 | CH₃ | S | * | 125.8 |
| 155 | 2-F—C₆H₄ | 5 | CH₃ | S | * | 165.8 |
| 156 | 4-C₂H₅—C₆H₄ | 3 | CH₃ | S | * | 176.6 |
| 157 | 3-CH₃O—C₆H₄ | 5 | CH₃ | S | * | 157.3 |
| 158 | 2,5-Cl₂—C₆H₃ | 3 | CH₃ | S | * | 171.7 |
| 159 | 2-CH₃CO—4-F—C₆H₃ | 3 | CH₃ | S | * | 144.7 |
| 160 | 3-F—C₆H₄ | 5 | CH₃ | S | * | 186.7 |
| 161 | 4-CH₃O—C₆H₄ | 4 | H | S | base | 95.4 |
| 162 | 4-F—C₆H₄ | 4 | H | S | base | 125.8 |
| 163 | 4-Cl—C₆H₄ | 4 | H | S | base | 149.8 |
| 164 | 4-Cl—C₆H₄ | 4 | C₂H₅ | S | * | 136.5 |
| 165 | 4-CH₃O—C₆H₄ | 4 | C₂H₅ | S | * | 125.1 |
| 166 | 4-F—C₆H₄ | 4 | C₂H₅ | S | (COOH)₂ | 163.9 |

| No. | Ar | s | R¹ | Z | base/salt | mp. in °C. |
|---|---|---|---|---|---|---|
| 167 | 3-F—C₆H₄ | 6 | CH₃ | S | *** | 155.9 |

*(Z)—2-butenedioate (1:1)
**(Z)—2-butenedioate (1:2)
***(E)—2-butenedioate (1:1)

In a similar manner there were also prepared:
N-[1-[3-(4-fluorophenoxy)-2-methylpropyl]-4-piperidinyl]-N-methyl-2-benzothiazolamine (Z)-2-butenedioate (1:1); mp. 143.6° C. (168);

5-methoxy-N-[1-[4-(4-methoxyphenoxy)butyl]-4-piperidinyl]-N-methyl-2-benzothiazolamine ethanedioate(1:1); mp. 98.2° C. (169);

N-(3-methyl-2(3H)-benzothiazolylidene-1-[3-(3-methylphenoxy)propyl]-4-piperidinamine (Z)-2-butenedioate(1:2); mp. 176.0° C. (170);

N-(3-methyl-2(3H)-benzothiazolylidene)-1-(4-phenoxybutyl)-4-piperidinamine (Z)-2-butenedioate(1:2); mp. 187.6° C. (171);

1-[4-(3-chlorophenoxy)butyl]-N-(3-methyl-2(3H)-benzothiazolylidene)-4-piperidinamine (Z)-2-butenedioate(1:2); mp. 164.6° C. (172);

1-[4-(4-fluorophenoxy)butyl]-N-(3-methyl-2(3H)-benzothiazolylidene)-4-piperidinamine (Z)-2-butenedioate(1:2); mp. 172.6° C. (173);

1-[4-(4-methoxyphenoxy)butyl]-N-(3-methyl-2(3H)-benzothiazolylidene)-4-piperidinamine (Z)-2-butenedioate(1:2); mp. 166.6° C. (174);

N-(3-methyl-2(3H)-benzothiazolylidene)-1-(3-phenyl-2-propenyl)-4-piperidinamine (Z)-2-butenedioate (1:2); mp. 179.4° C. (175);

5-bromo-N-[1-[4-(4-fluorophenoxy)butyl]-4-piperidinyl]-6-methoxy-N-methyl-2-benzothiazolamine; mp. 124.6° C. (176);

N-[1-[3-(3-fluorophenoxy)propyl]-4-piperidinyl]-5-methoxy-N-methyl-2-benzothiazolamine (Z)-2-butenedioate(1:1); mp. 126.3° C. (177).

EXAMPLE 26

A mixture of 2.3 parts of [2-(4-methoxyphenyl)ethyl]methanesulfonate, 4 parts of N-(4-piperidinyl)-2-benzothiazolamine dihydrobromide, 5.3 parts of sodium carbonate, 0.1 parts of potassium iodide and 90 parts of N,N-dimethylformamide was stirred overnight at 70° C. The reaction mixture was poured onto water and the product was extracted with methylbenzene. The extract was washed with water, dried, filtered and evaporated. The residue was crystallized from a mixture of 2-propanol and 2,2'-oxybispropane. The product was filtered off and dried, yielding 1.5 parts (41%) of N-[1-[2-(4-methoxyphenyl)ethyl]-4-piperidinyl]-2-benzothiazolamine; mp. 142.5° C. (178).

In a similar manner there were also prepared:
N-[1-[2-(4-methoxyphenyl)ethyl]-4-piperidinyl]-N-methyl-2-benzothiazolamine; mp. 97.6° C. (179); and
N-[1-[2-(4-methoxyphenyl)ethyl]-4-piperidinyl]-thiazolo[5,4-b]pyridin-2-amine; mp. 158.9° C. (180).

EXAMPLE 27

A mixture of 4.3 parts of 1-(4-chlorobutoxy)-4-methoxybenzene, 6.6 parts of N-(phenylmethyl)-N-(4-piperidinyl)-2-benzothiazolamine (Z)-2-butenedioate(1:1), 5.3 parts of sodium carbonate, 0.1 parts of potassium iodide and 90 parts of N,N-dimethylacetamide was stirred overnight at 90° C. The reaction mixture was poured onto water. The product was extracted with methylbenzene. The extract was washed with water, dried, filtered and evaporated. The residue was converted into the (E)-2-butenedioate salt in ethanol. The salt was filtered off and dried, yielding 5.6 parts (60%) of N-[1-[4-(4-methoxyphenoxy)butyl]-4-piperidinyl]-N-(phenylmethyl)-2-benzothiazolamine (E)-2-butenedioate(1:1); mp. 178.2° C. (181).

In a similar manner there were also prepared:

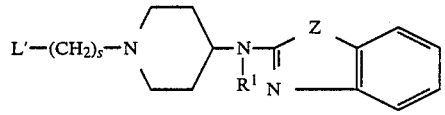

| No. | L' | s | Z | base/salt | mp. in °C. |
|---|---|---|---|---|---|
| 182 | H | 12 | S | * | 161.4 |
| 183 | 3-oxo-1,2,4-triazolo[4,5-a]pyridin-2-yl | 3 | S | * | 185.0 |
| 184 | 4-F—C$_6$H$_4$—CH(CN)— | 3 | O | 1½(COOH)$_2$ | 139.5 |
| 185 | (C$_6$H$_5$)$_2$CH—O— | 2 | O | * | 175.3 |
| 186 | HO | 2 | O | * | 172.6 |
| 187 | C$_6$H$_5$—NH— | 3 | S | 2½(COOH)$_2$ | 177.1 |

-continued

| No. | L' | s | Z | base/salt | mp. in °C. |
|---|---|---|---|---|---|
| 188 | 2,3-dihydro-1,4-benzodioxin-2-yl | 2 | O | * | 182.1 |
| 189 | C$_6$H$_5$—NH— | 2 | O | * | 152.6 |
| 190 | 2,3-dihydro-1,4-benzodioxin-2-yl | 2 | S | * | 168.6 |

*(Z)—2-butenedioate (1:1)

In a similar manner there were also prepared:

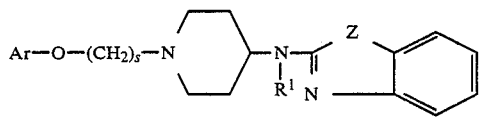

| No. | Ar | s | R$^1$ | Z | base/salt | mp. in °C. |
|---|---|---|---|---|---|---|
| 191 | 3-Cl—C$_6$H$_4$— | 5 | CH$_3$ | S | * | 177.7 |
| 192 | 4-CH$_3$—C$_6$H$_4$— | 5 | CH$_3$ | S | * | 165.1 |
| 193 | 2-F—C$_6$H$_4$— | 3 | CH$_3$ | O | * | 208.0 |
| 194 | 3,5-Cl$_2$—C$_6$H$_3$— | 3 | CH$_3$ | S | * | 178.1 |
| 195 | 3-F—C$_6$H$_4$— | 3 | CH$_3$ | O | * | 180.6 |
| 196 | 3-F—C$_6$H$_4$— | 4 | CH$_3$ | S | * | 143.8 |
| 197 | 3-F—C$_6$H$_4$— | 4 | CH$_3$ | O | * | 158.8 |
| 198 | C$_6$H$_5$— | 4 | C$_6$H$_5$CH$_2$ | S | * | 129.9 |
| 199 | 4-CH$_3$—C$_6$H$_4$— | 3 | C$_6$H$_5$CH$_2$ | S | ** | 198.4 |
| 200 | 4-Cl—C$_6$H$_4$— | 4 | C$_6$H$_5$CH$_2$ | S | * | 149.5 |
| 201 | 3-F—C$_6$H$_4$— | 3 | C$_6$H$_5$CH$_2$ | S | * | 145.1 |
| 202 | 4-F—C$_6$H$_4$— | 4 | C$_6$H$_5$CH$_2$ | S | * | 153.6 |
| 203 | 4-NO$_2$—C$_6$H$_4$— | 4 | CH$_3$ | S | * | 169.7 |

*(Z)—2-butenedioate (1:1)
**(E)—2-butenedioate (1:1)

In a similar manner there was also prepared: 1-[3-(3-fluorophenoxy)propyl]-N-(3-methyl-2(3H)-benzothiazolylidene)-4-piperidinamine (Z)-2-butenedioate(1:2); mp. 173.4° C. (204).

EXAMPLE 28

A mixture of 5.5 parts of cis-N-(3-methoxy-4-piperidinyl-N-methyl-2-benzothiazolamine ethanedioate(1:1), 10.6 parts of sodium carbonate, 0.1 parts of potassium iodide and 200 parts of 4-methyl-2-pentanone was stirred and refluxed for 30 minutes. After cooling to 60° C., 4.4 parts of 1-chloro-4-(4-chlorobutoxy)benzene were added. The whole was stirred and refluxed overnight. After cooling, water was added and the layers were separated. The organic layer was dried, filtered and evaporated. The residue was purified by column chromatography over silica gel using a mixture of trichloromethane and methanol (98:2 by volume) as eluent. The pure fractions were collected and the eluent was evaporated. The residue was converted into the ethanedioate salt in 2-propanol. The salt was filtered off and dried, yielding 6 parts (73%) of cis-N-[1-[4-(4-chlorophenoxy)butyl]-3-methoxy-4-piperidinyl]-N-methyl-2-benzothiazolamine ethanedioate(1:1); mp. 210.4° C. (205).

In a similar manner there were also prepared:

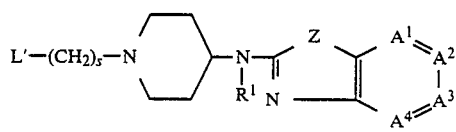

| No. | L' | s | R¹ | z | A¹=A²—A³=A⁴ | base salt | mp in °C. |
|---|---|---|---|---|---|---|---|
| 206 | 3-oxo-1,2,4-triazolo-[4,3-a]pyridin-2-yl | 3 | CH₃ | S | N=CH—CH=CH | 2HCl ½H₂O | 235.5 |
| 207 | cyclohexyloxy | 3 | CH₃ | S | CH=CH—CH=CH | * | 160.2 |
| 208 | 4-F—C₆H₄—CH=CH— | 2 | CH₃ | S | CH=CH—CH=CH | * | 145.0 |
| 209 | 3,4-dihydro-2H—1-benzopyran-2-yl | 1 | CH₃ | O | CH=CH—CH=CH | (COOH)₂ | 212.1 |
| 210 | 3,4-dihydro-2H—1-benzopyran-2-yl | 1 | CH₃ | S | CH=CH—CH=CH | base | 129.8 |
| 211 | C₆H₅—CH=CH— | 1 | H | S | CH=CH—CH=CH | ** | 177.8 |
| 212 | C₆H₅—CH=CH— | 1 | n.C₃H₇ | S | CH=CH—CH=CH | *** | 165.4 |
| 213 | 2-pyridinyl- | 2 | CH₃ | S | CH=CH—CH=CH | ** | 139.5 |
| 214 | C₆H₅—CH=CH— | 1 | CH₃ | S | CH=C(CH₃)—CH=CH | * | 177.3 |
| 215 | 3-phenyl-5-isoxazolyl | 2 | CH₃ | S | CH=CH—CH=CH | * | 178.8 |
| 216 | 4-F—C₆H₄— | 4 | CH₃ | S | CH=CH—CH=CH | (COOH)₂ | 150.3 |
| 217 | H | 9 | CH₃ | S | CH=CH—CH=CH | * | 165.2 |
| 218 | C₆H₅—CH=CH | 1 | CH₃ | S | CH=CF—CH=CH | * | 174.6 |
| 219 | C₆H₅—CH=CH | 1 | CH₃ | S | CH=CH—CF=CH | * | 201.7 |
| 220 | C₆H₅—CH=CH | 1 | CHCH | S | CH=CH—CH=CH | * | 212.6 |
| 221 | C₆H₅—CH=CH | 1 | (CH₃)CH | S | CH=CH—CH=CH | * | 170.5 |
| 222 | C₆H₅—CH=CH | 1 | CH₃ | S | CH=CCl—CH=CH | base | 130.0 |
| 223 | C₆H₅—CH=CH | 1 | CH₃ | S | CH=CH—CCl=CH | * | 189.8 |
| 224 | C₆H₅—CH=CH | 1 | CH₃ | S | CCl=CH—CH=CH | * | 213.5 |

*: (Z)—2-butenedioate (1:1)
**: (Z)—2-butenedioate (1:2)
***: (E)—2-butenedioate (1:1)

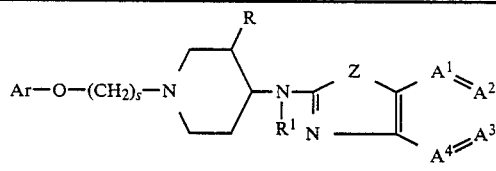

| No. | Ar | s | R | R¹ | Z | A¹=A²—A³=A⁴ | cis/trans | base salt | mp in °C. |
|---|---|---|---|---|---|---|---|---|---|
| 225 | 2-CH₃OCO—C₆H₄ | 3 | H | CH₃ | S | CH=CH—CH=CH | — | * | 177.0 |
| 226 | 4-F—C₆H₄ | 6 | H | CH₃ | S | CH=CH—CH=CH | — | * | 140.0 |
| 227 | C₆H₅ | 5 | H | CH₃ | S | CH=CH—CH=CH | — | * | 179.9 |
| 228 | 2-n.C₃H₇C₆H₄ | 3 | H | CH₃ | S | CH=CH—CH=CH | — | * | 164.8 |
| 229 | 3-F—C₆H₄ | 3 | OCH₃ | CH₃ | S | CH=CH—CH=CH | cis | *** | 210.5 |
| 230 | 3-CH₃—C₆H₄ | 3 | H | CH₃ | S | CH=CF—CH=CH | — | base | 90.6 |
| 231 | 3-F—C₆H₄ | 3 | H | CH₃ | S | CH=C(CH₃)—CH=CH | — | * | 140.7 |
| 232 | 3-CH₃—C₆H₄ | 3 | H | CH₃ | S | CH=C(CH₃)—CH=CH | — | * | 165.6 |
| 233 | C₆H₅ | 4 | H | CH₃ | S | CH=C(CH₃)—CH=CH | — | * | 141.4 |
| 234 | 4-CH₃O—C₆H₄ | 4 | H | CH₃ | S | CH=CF—CH=CH | — | base | 90.7 |
| 235 | 3-F—C₆H₄ | 3 | H | CH₃ | S | CH=CF—CH=CH | — | * | 171.1 |
| 236 | C₆H₅ | 4 | H | CH₃ | S | CH=CF—CH=CH | — | * | 142.7 |
| 237 | 4-CH₃O—C₆H₄ | 4 | H | CH₃ | S | CH=C(CH₃)—CH=CH | — | * | 123.8 |

-continued

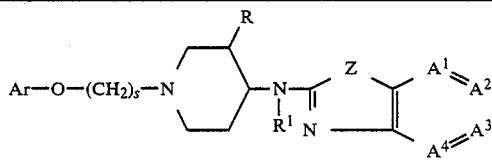

| No. | Ar | s | R | $R^1$ | Z | $A^1=A^2-A^3=A^4$ | cis/trans | base salt | mp in °C. |
|---|---|---|---|---|---|---|---|---|---|
| 238 | 3-F—$C_6H_4$ | 3 | H | i.$C_3H_7$ | S | CH=CH—CH=CH | — | * | 160.1 |
| 239 | 4-F—$C_6H_4$ | 4 | H | i.$C_3H_7$ | S | CH=CH—CH=CH | — | * | 161.1 |
| 240 | 4-Cl—$C_6H_4$ | 4 | H | i.$C_3H_7$ | S | CH=CH—CH=CH | — | * | 149.7 |
| 241 | 4-$CH_3$—$C_6H_4$ | 3 | H | i.$C_3H_7$ | S | CH=CH—CH=CH | — | base | 99.2 |
| 242 | 3-F—$C_6H_4$ | 3 | H | $CH_3$ | S | CH=CH—CCl=CH | — | * | 153.8 |
| 243 | 4-$CH_3O$—$C_6H_4$ | 4 | H | i.$C_3H_7$ | S | CH=CH—CH=CH | — | * | 158.7 |
| 244 | $C_6H_5$ | 4 | H | i.$C_3H_7$ | S | CH=CH—CH=CH | — | * | 136.2 |
| 245 | 3-F—$C_6H_4$ | 3 | H | $CH_3$ | S | CCl=CH—CH=CH | — | * | 181.2 |
| 246 | 3-$CH_3$—$C_6H_4$ | 3 | H | $CH_3$ | S | CH=CH—C(OCH$_3$)=CH | — | ** | 161.2 |
| 247 | $C_6H_5$ | 4 | $OCH_3$ | $CH_3$ | S | CH=CH—CH=CH | cis | **** | 198.3 |
| 248 | 3-$CH_3$—$C_6H_4$ | 3 | $OCH_3$ | $CH_3$ | S | CH=CH—CH=CH | cis | **** | 187.2 |
| 249 | 4-$CH_3O$—$C_6H_4$ | 4 | $OCH_3$ | $CH_3$ | S | CH=CH—CH=CH | cis | **** | 214.6 |
| 250 | 3-$CH_3$—$C_6H_4$ | 3 | H | $CH_3$ | S | CH=CH—CCl=CH | — | * | 151.0 |
| 251 | 3-$CH_3$—$C_6H_4$ | 3 | H | $CH_3$ | S | CCl=CH—CH=CH | — | * | 178.4 |
| 252 | 4-$CH_3O$—$C_6H_4$ | 4 | H | $CH_3$ | S | CH=CH—CF=CH | — | * | 157.2 |
| 253 | 4-$CH_3O$—$C_6H_4$ | 4 | H | $CH_3$ | S | CCl=CH—CH=CH | — | * | 171.1 |
| 254 | 3-$CH_3$—$C_6H_4$ | 3 | H | $CH_3$ | S | CH=CH—CF=CH | — | * | 163.8 |
| 255 | $C_6H_5$ | 4 | H | $CH_3$ | S | CH=CH—CF=CH | — | * | 185.1 |
| 256 | 3-F—$C_6H_4$ | 3 | H | $CH_3$ | S | CH=CH—CF=CH | — | * | 167.9 |
| 257 | $C_6H_5$ | 4 | H | $CH_3$ | S | CH=CH—CCl=CH | — | * | 200.4 |
| 258 | 4-$CH_3O$—$C_6H_4$ | 4 | H | $CH_3$ | S | CH=CH—CCl=CH | — | * | 143.1 |
| 259 | $C_6H_5$ | 4 | H | $CH_3$ | S | CCl=CH—CH=CH | — | * | 176.8 |
| 260 | 4-Cl—$C_6H_4$ | 4 | H | H | O | CH=CH—CH=CH | — | 2HCl | 251.2 |
| 261 | 4-F—$C_6H_4$ | 4 | H | H | O | CH=CH—CH=CH | — | 2HCl | 239.8 |
| 262 | 4-$CH_3$—$C_6H_4$ | 3 | H | H | O | CH=CH—CH=CH | — | 2HCl | 246.6 |
| 263 | 4-$CH_3O$—$C_6H_4$ | 4 | H | H | O | CH=CH—CH=CH | — | 2HCl | 237.3 |
| 264 | 3-$CH_3$—$C_6H_4$ | 3 | H | H | O | CH=CH—CH=CH | — | 2HCl.$H_2O$ | 219.2 |
| 265 | 3-Cl—$C_6H_4$ | 4 | H | H | O | CH=CH—CH=CH | — | 2HCl | 217.3 |
| 266 | $C_6H_5$ | 4 | H | H | O | CH=CH—CH=CH | — | 2HCl.½$H_2O$ | 231.7 |
| 267 | 3-F—$C_6H_4$ | 3 | H | H | O | CH=CH—CH=CH | — | 2HCl.$H_2O$ | 224.8 |
| 268 | $C_6H_5$ | 4 | OH | H | S | CH=CH—CH=CH | cis | base | 158.2 |
| 269 | 3-$CH_3$—$C_6H_4$ | 3 | OH | H | S | CH=CH—CH=CH | cis | base | 146.9 |
| 270 | 4-Cl—$C_6H_4$ | 4 | OH | H | S | CH=CH—CH=CH | cis | base | 179.7 |
| 271 | 3-F—$C_6H_4$ | 3 | OH | H | S | CH=CH—CH=CH | cis | base | 165.8 |

*: (Z)—2-butenedioate(1:1)
**: (E)—2-butenedioate(1:1)
***: ethanedioate (1:1) hemihydrate
****: ethanedioate (1:1)

In a similar manner there were also prepared:
N-methyl-N-[1-[2-(phenylmethoxy)propyl]-4-piperidinyl]-2-benzothiazolamine (Z)-2-butenedioate (1:1); mp. 150.5° C. (272);
N-methyl-N-[1-(2-methyl-3-phenoxypropyl)-4-piperidinyl]-2-benzothiazolamine (Z)-2-butenedioate (1:1); mp. 177.0° C. (273);
N-methyl-N-[1-[2-(3-methylphenoxy)propyl]-4-piperidinyl]-2-benzothiazolamine (Z)-2-butenedioate (1:1); mp. 168.6° C. (274);
N-[1-[2-(2,6-dimethylphenoxy)propyl]-4-piperidinyl]-N-methyl-2-benzothiazolamine (Z)-2-butenedioate (1:1); mp. 130.4° C. (275);
N-[1-[2-(2,6-dichlorophenoxy)propyl]-4-piperidinyl]-N-methyl-2-benzothiazolamine; mp. 108.0° C. (276);
N-[1-[2-(3,5-dimethylphenoxy)propyl]-4-piperidinyl]-N-methyl-2-benzothiazolamine (Z)-2-butenedioate (1:1); mp. 172° C. (277);
N-(2-benzothiazolyl)-8-[3-(3-fluorophenoxy)propyl]-N-methyl-8-azabicyclo[3.2.1]octan-3-amine (E)-2-butenedioate(1:1); mp. 171.3° C. (278);
(E)-N-methyl-N-[8-(3-phenyl-2-propenyl)-8-azabicyclo[3.2.1]oct-3-yl]-2-benzothiazolamine ethanedioate(1:1); mp. 216.0° C. (279);
N-(2-benzothiazolyl)-N-methyl-8-(4-phenoxybutyl)-8-azabicyclo[3,2,1]octan-3-amine (E)-2-butenedioate(1:1); mp. 158.0° C. (280);
cis-N-methyl-N-[3-methyl-1-(3-phenyl-2-propenyl)-4-piperidinyl]-2-benzothiazolamine (Z)-2-butenedioate (1:1); mp. 173.7° C. (281);
cis-N-[3-methoxy-1-(3-phenyl-2-propenyl)-4-piperidinyl]-N-methyl-2-benzothiazolamine ethanedioate(1:1); mp. 230.2° C. (282);
N-(2-benzothiazolyl)-N-methyl-8-[3-(3-methoxyphenoxy)propyl]-8-azabicyclo[3.2.1]octan-3-amine ethanedioate(1:1); mp. 183.3° C. (283);

N-methyl-N-[1-(4-phenoxybutyl)-3-piperidinyl]-2-benzothiazolamine ethanedioate(1:1); mp. 152.5° C. (284);

N-[1-[3-(3-fluorophenoxy)propyl]-3-piperidinyl]-N-methyl-2-benzothiazolamine ethanedioate(1:1); mp. 164.5° C. (285);

N-methyl-N-[1-(3-phenyl-2-propenyl)-3-piperidinyl]-2-benzothiazolamine ethanedioate(1:1); mp. 202.8° C. (286);

N-methyl-N-[1-[3-(3-methylphenoxy)propyl]-3-piperidinyl]-2-benzothiazolamine ethanedioate(1:1); mp. 151.3° C. (287);

N-[1-[4-(4-methoxyphenoxy)butyl]-3-piperidinyl]-N-methyl-2-benzothiazolamine ethanedioate(1:1); mp. 152.3° C. (288);

N-[1-[4-(4-fluorophenoxy)butyl]-3-piperidinyl-N-methyl-2-benzothiazolamine ethanedioate(1:1); mp. 163.2° C. (289);

N-[1-[3-(4-fluorophenoxy)-1-methylpropyl]-4-piperidinyl]-N-methyl-2-benzothiazolamine; mp. 115.0° C. (290);

N-[1-[4-(3-chlorophenoxy)butyl]-3-piperidinyl]-N-methyl-2-benzothiazolamine (E)-2-butenedioate(1:1); mp. 138.6° C. (291);

N-methyl-N-[1-(3-phenyl-2-propenyl)-3-pyrrolidinyl]-2-benzothiazolamine 4-methylbenzenesulfonate(1:2); mp. 198.8° C. (292); and cis-4-(2-benzothiazolylamino)-1-(3-phenyl-2-propenyl)-3-piperidinol; mp. 198.3° C. (293).

EXAMPLE 29

A mixture of 3 parts of 1-bromo-3-methylbutane, 3.7 parts of N-methyl-N-(4-piperidinyl)-1-benzothiazolamine, 4.2 parts of potassium carbonate and 80 parts of 2-propanone was stirred and refluxed overnight. The reaction mixture was poured onto water and the product was extracted with methylbenzene. The extract was dried, filtered and evaporated. The residue was converted into the (Z)-2-butenedioate salt in 2-propanol. The salt was filtered off and dried, yielding 5 parts (77%) of N-methyl-N-[1-(3-methylbutyl)-4-piperidinyl]-2-benzothiazolamine (Z)-2-butenedioate (1:1); mp. 197.2° C. (294).

EXAMPLE 30

A mixture of 3 parts of (3-chloro-1propenyl)benzene, 2.6 parts of 2-[methyl(4-piperidinyl)amino]-5-benzothiazolol, 3.5 parts of N,N-diethylethanamine and 90 parts of N,N-dimethylformamide was stirred and heated for 24 hours at 60° C. The reaction mixture was cooled, poured onto water and the product was extracted with methylbenzene. The extract was washed with water, dried, filtered and evaporated. The residue was purified by column chromatography over silica gel using a mixture of trichloromethane and methanol (97:3 by volume) as eluent. The pure fractions were collected and the eluent was evaporated. The residue was converted into the (E)-2-butenedioate salt in ethanol. The salt was filtered off and dried, yielding 1 part (20%) of 2-[methyl[1-(3-phenyl-2-propenyl)-4-piperidinyl]amino]-5-benzothiazolol (E)-2-butenedioate(1:1); mp. 228.4° C. (295).

EXAMPLE 31

To a stirred mixture of 1.1 parts of a sodium hydride dispersion 50% and 45 parts of N,N-dimethylformamide were added 3.1 parts of 4-[(2-benzothiazolyl)methylamino]-1-piperidinepropanol and the whole was stirred and heated for 2 hours at about 60° C. After cooling to about 15° C., 1.65 parts of 4-chloropyridine hydrochloride were added and stirring was continued overnight at 60° C. The reaction mixture was cooled and the solvent was evaporated. The residue was taken up in water and extracted with methylbenzene. The extract was dried, filtered and evaporated. The residue was purified by filtration over silica gel using a mixture of trichloromethane and methanol (98:2 by volume) as eluent. The pure fractions were collected and the eluent was evaporated. The residue was crystallized from 2,2'-oxybispropane, yielding, after drying, 1.5 parts (38%) of N-methyl-N-[1-[3-(4-pyridinyloxy)propyl]-4-piperidinyl]-2-benzothiazolamine monohydrate; mp. 96.3° C. (296).

EXAMPLE 32

A mixture of 4.75 parts of cyclopentanone, 4.1 parts of N-(1-methylethyl)-N-(4-piperidinyl)-2-benzothiazolamine and 200 parts of methanol was hydrogenated at normal pressure and at room temperature with 2 parts of palladium-on-charcoal catalyst 10%. After the calculated amount of hydrogen was taken up, the catalyst was filtered off over Hyflo and the filtrate was evaporated. The residue was purified by column chromatography over silica gel using a mixture of trichloromethane and methanol (98.5:1.5 by volume) as eluent. The pure fractions were collected and the eluent was evaporated. The residue was converted into the (Z)-2-butenedioate salt in 2-propanol. The salt was filtered off and dried, yielding 3.9 parts (56.6%) of N-(1-cyclopentyl-4-piperidinyl)-N-(1-methylethyl)-2-benzothiazolamine (Z)-2-butenedioate(1:1); mp. 178.5° C. (297).

In a similar manner there were also prepared:

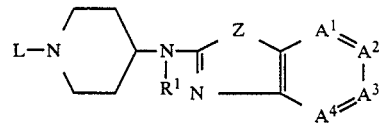

| No. | L | $R^1$ | Z | $A^1=A^2-A^3=A^4$ | base salt | mp in °C. |
|---|---|---|---|---|---|---|
| 298 | $CH_3$ | H | S | CH=CH—CH=CH | 2HCl.½H$_2$O | 283.1 |
| 299 | $CH_3$ | H | S | N=CH—CH=CH | base | 170.6 |
| 300 | $CH_3$ | $CH_3$ | S | N=CH—CH=CH | 2HCl | 266.5 |
| 301 | cyclohexyl | H | O | CH=CH—CH=CH | base | 137.4 |
| 302 | $CH_3$ | H | O | CH=CH—CH=CH | base | 132.1 |
| 303 | $C_2H_5$ | $CH_3$ | O | CH=CH—CH=CH | 2HBr.H$_2$O | 240.9 |
| 304 | $CH_3$ | $CH_3$ | O | CH=CH—CH=CH | 2HNO$_3$ | 142.9 |
| 305 | i.$C_3H_7$ | $CH_3$ | S | CH=CH—CH=CH | 2HCl.H$_2$O | 265.9 |

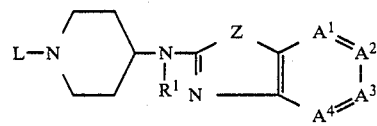

| No. | L | R¹ | Z | A¹=A²—A³=A⁴ | base salt | mp in °C. |
|---|---|---|---|---|---|---|
| 306 | cyclohexyl | CH₃ | S | CH=CH—CH=CH | 2HCl | 278.8 |
| 307 | cyclopentyl | CH₃ | S | CH=CH—CH=CH | 2HCl | 268.8 |
| 308 | cyclopentyl | CH₃ | O | CH=CH—CH=CH | 2HCl.2H₂O | 276.2–280.8(dec) |
| 309 | cyclohexyl | (CH₃ | O | CH=CH—CH=CH | 2HCl.H₂O | 300 |
| 310 | cyclopropylmethyl | CH₃ | S | CH=CH—CH=CH | 2HCl | 236.4 |
| 311 | cyclopentyl | H | S | CH=CH—CH=CH | base | 172.7 |
| 312 | cyclopentyl | C₂H₅ | S | CH=CH—CH=CH | * | 145.1 |
| 313 | cyclopentyl | n.C₄H₉ | S | CH=CH—CH=CH | ** | 181.6 |
| 314 | cyclopentyl | C₆H₅CH₂ | S | CH=CH—CH=CH | * | 202.1 |
| 315 | cyclopropylmethyl | CH₃ | O | CH=CH—CH=CH | * | 184.9 |

*(Z)—2-butenedioate (1:1)
**(E)—2-butenedioate (1:1)

In a similar manner there were also prepared:
cis-4-[4-[(2-benzothiazolyl)methylamino]-1-piperidinyl]-1(4-fluorophenyl)cyclohexanecarbonitrile; mp. 184.7° C. (316);
(cis+trans)-N-[1-[4-(4-fluorophenoxy)cyclohexyl]-4-piperidinyl]-N-methyl-2-benzothiazolamine; mp. 198.4° C. (317);
cis-4-[4-[(2-benzoxazolyl)methylamino]-1-piperidinyl]-1-(4-fluorophenyl)cyclohexanecarbonitrile; mp. 199.6° C. (318); and
N-[1-(1H-indol-3-ylmethyl)-4-piperidinyl]-N-methyl-2-benzothiazolamine; mp. 178.3° C. (319).

EXAMPLE 33

A mixture of 2.5 parts of [(4-fluorophenoxy)methyl]oxirane, 3.7 parts of N-methyl-N-(4-piperidinyl)-2-benzothiazolamine, 45 parts of methylbenzene and 40 parts of methanol was stirred and refluxed for 24 hours. The reaction mixture was evaporated. The residue was converted into the hydrochloride salt in 2-propanol. The salt was filtered off and dried, yielding 6 parts (85%) of 4-[(2-benzothiazolyl)methylamino]-α-[(4-fluorophenoxy)methyl]-1-piperidineethanol monohydrochloride; mp. 168.4°–178.8° C. (320).

Following the same procedure and using equivalent amounts of the appropriate starting materials, there were also prepared:

| No. | Ar | R¹ | Z | base/salt | mp. in °C. |
|---|---|---|---|---|---|
| 321 | C₆H₅ | H | O | base | 119.8 |
| 322 | C₆H₅ | CH₃ | O | HBr | 231.6 |
| 323 | 4-F—C₆H₄ | CH₃ | O | HCl | 233.5 |
| 324 | 4-Cl—C₆H₄ | CH₃ | O | HCl | 237.5 |
| 325 | 2-C₂H₅O—C₆H₄ | CH₃ | O | 2HCl | 203.3 |
| 326 | 2-propenyloxyphenyl | CH₃ | O | HCl | 144.6 |
| 327 | 4-CH₃CONH—C₆H₄ | CH₃ | O | 2HCl | 236.0 |
| 328 | 4-CH₃CONH—C₆H₄ | CH₃ | S | 2HCl | 169.6–182.2 |
| 329 | 1-naphthalenyl | CH₃ | S | (COOH)₂ | 198.1–199.9 |
| 330 | 2-propenyloxyphenyl | CH₃ | S | (COOH)₂ | 120.3–129.5 |
| 331 | 4-Cl—C₆H₄ | CH₃ | S | 2HCl | 206.0–225.6 |
| 332 | 1-naphthalenyl | CH₃ | O | (COOH)₂ | 232.1–233.1 |
| 333 | 2-acetylphenyl | CH₃ | O | (COOH)₂ | 203.2–203.6 |
| 334 | 2-acetylphenyl | CH₃ | S | (COOH)₂ | 222.8–223.1 |
| 335 | 2-C₂H₅O—C₆H₄ | CH₃ | S | (COOH)₂ H₂O | 112.9–118.6 |
| 336 | 2-Cl—C₆H₄ | CH₃ | S | (COOH)₂ ½H₂O | 180.9–182.8 |
| 337 | 2-Cl—C₆H₄ | CH₃ | O | (COOH)₂ ½H₂O | 172.6–182.1 |
| 338 | C₆H₅ | CH₃ | S | (COOH)₂ | 166.0–169.6 |
| 339 | 2-CN—C₆H₄ | CH₃ | O | (COOH)₂ | 173.9–175.6 |
| 340 | 2-CN—C₆H₄ | CH₃ | S | * | 150.5 |
| 341 | 3-Cl—C₆H₄ | CH₃ | S | base | 129.0 |
| 342 | 2,4-Cl₂—C₆H₃ | CH₃ | O | * | 187.7 |
| 343 | 2,4-Cl₂—C₆H₃ | CH₃ | S | * | 167.8 |
| 344 | 3-CF₃—C₆H₄ | CH₃ | S | 2HCl | 220.9 |
| 345 | 2,3-dihydro-1H—inden-5-yl | CH₃ | S | base | 95.9 |
| 346 | 2-Br—C₆H₄ | CH₃ | S | * | 167.0 |

-continued

Ar—O—CH$_2$—CH(OH)—CH$_2$—N(piperidine)—N(R$^1$)—C(=N)—Z—[benzene with Z attachment]

| No. | Ar | R$^1$ | Z | base/salt | mp. in °C. |
|---|---|---|---|---|---|
| 347 | 6-Br—2-napthalenyl | CH$_3$ | S | * | 192.9 |
| 348 | 4-Cl,3,5-(CH$_3$)$_2$C$_6$H$_2$ | CH$_3$ | S | base | 131.7 |
| 349 | 4-(4-methylbenzoyl)phenyl | CH$_3$ | S | base | 174.2 |
| 350 | 2,4,6-(Cl$_2$)$_3$—C$_6$H$_2$ | CH$_3$ | S | base | 126.4 |
| 351 | 2,6-(CH$_3$)$_2$—C$_6$H$_2$ | CH$_3$ | S | base | 146.8 |
| 352 | 3-CH$_3$O—C$_6$H$_4$ | CH$_3$ | S | ** | 118.5 |
| 353 | 2-n.C$_3$H$_7$—CO—C$_6$H$_4$ | CH$_3$ | S | (COOH)$_2$ | 159.0 |
| 354 | 3-Cl—C$_6$H$_4$ | CH$_3$ | O | * | 123.7 |
| 355 | 4-Cl—C$_6$H$_4$ | H | S | base | 164.8 |
| 356 | 4-F—C$_6$H$_4$ | H | S | base | 162.8 |
| 357 | 4-Cl—C$_6$H$_4$ | C$_2$H$_5$ | S | base | 103.1 |
| 358 | 4-F—C$_6$H$_4$ | C$_2$H$_5$ | S | *** | 205.7 |
| 359 | 4-Cl,2-CH$_3$—C$_6$H$_3$ | CH$_3$ | S | base | 115.5 |
| 360 | 2-F—C$_6$H$_4$ | CH$_3$ | S | base | 100.4 |
| 361 | 2-CH$_3$CO,4-F—C$_6$H$_3$ | CH$_3$ | S | base | 108.7 |
| 362 | 4-F—C$_6$H$_4$ | CH$_3$ | S | *** | 169.5 |
| 363 | 4-CH$_3$CO—C$_6$H$_4$ | CH$_3$ | S | base | 98.9 |
| 364 | 4-F—C$_6$H$_4$ | i.C$_3$H$_7$ | S | * | 161.8 |
| 365 | 4-F—C$_6$H$_4$ | CH$_3$ | S | base | 101.7 |
| 336 | 4-Cl—C$_6$H$_4$ | i.C$_3$H$_7$ | S | * | 169.8 |
| 367 | 4-CN—C$_6$H$_4$ | CH$_3$ | S | base | 122.1 |
| 368 | C$_6$H$_5$ | CH$_3$ | S | * | 135.6 |
| 369 | 4-F—C$_6$H$_4$ | CH$_3$ | S | 2HCl | 209.4 |
| 370 | 4-NO$_2$—C$_6$H$_4$ | CH$_3$ | S | base | 140.1 |
| 371 | 4-F—C$_6$H$_4$ | H | O | 2HCl | 227.9 |
| 372 | 3-Cl—C$_6$H$_4$ | H | O | 2HCl | 213.2 |
| 373 | 3,4,5-(CH$_3$O)$_3$C$_6$H$_2$ | CH$_3$ | S | * | 176.9 |
| 374 | 4-CH$_3$O—C$_6$H$_4$ | CH$_3$ | S | base | 129.6 |
| 375 | 3,5-(CH$_3$O)$_2$—C$_6$H$_3$ | CH$_3$ | S | * | 145.2 |
| 376 | 1,3-benzodioxol-5-yl | CH$_3$ | S | *** | 181.7 |

*: (Z)—2-butenedioate (1:1)
**: (Z)—2-butenedioate (1:2)
***: (E)—2-butenedioate (2:1)

In a similar manner there were also prepared:

In a similar manner there were also prepared:

Ar—O—CH$_2$—C(OH)—CH$_2$—N(piperidine with R substituent)—N(R$^1$)—C(=N)—S—[ring with A$^1$=A$^2$—A$^3$=A$^4$]

| No. | Ar | R | R$^1$ | A$^1$=A$^2$—A$^3$=A$^4$ | cis/trans | base salt | mp in °C. |
|---|---|---|---|---|---|---|---|
| 377 | C$_6$H$_5$ | CH$_3$O | CH$_3$ | CH=CH—CH=CH | cis | * | 163.6 |
| 378 | 4-F—C$_6$H$_4$ | H | CH$_3$ | CH=CF—CH=CH | — | base | 101.5 |
| 379 | C$_6$H$_5$ | H | CH$_3$ | CH=CF—CH=CH | — | base | 130.6 |
| 380 | 4-F—C$_6$H$_4$ | CH$_3$O | CH$_3$ | CH=CH—CH=CH | cis | * | 178.9 |
| 381 | 4-F—C$_6$H$_4$ | CH$_3$ | CH$_3$ | CH=CH—CH=CH | cis | * | 150.0 |
| 382 | C$_6$H$_5$ | CH$_3$ | CH$_3$ | CH=CH—CH=CH | cis | * | 165.1 |
| 383 | 4-F—C$_6$H$_4$ | H | CH$_3$ | CH=CH—CF=CH | — | base | 118.1 |
| 384 | 4-F—C$_6$H$_4$ | H | CH$_3$ | CCl=CH—CH=CH | — | * | 154.0 |
| 385 | 4-F—C$_6$H$_4$ | H | CH$_3$ | CH=CH—CCl=CH | — | * | 144.6 |
| 386 | 4-F—C$_6$H$_4$ | H | H | N=CH—CH=CH | — | base | 168.2 |
| 387 | C$_6$H$_5$ | H | CH$_3$ | CH=CCl—CH=CH | — | base | 177.4 |
| 388 | 4-F—C$_6$H$_4$ | H | CH$_3$ | CH=CCl—CH=CH | — | base | 172.7 |
| 389 | 4-F—C$_6$H$_4$ | H | CH$_3$ | CH=CH—C(OCH$_3$)=CH | — | ** | 176.1 |
| 390 | C$_6$H$_5$ | H | CH$_3$ | CCl=CH—CH=CH | — | * | 174.8 |
| 391 | C$_6$H$_5$ | H | CH$_3$ | CH=CH—CCl=CH | — | * | 171.1 |
| 392 | 4-F—C$_6$H$_4$ | H | CH$_3$ | N=CH—CH=CH | — | base | 103.6 |
| 393 | 3-Cl—C$_6$H$_4$ | H | CH$_3$ | N=CH—CH=CH | — | base | 119.9 |

*: (Z)—2-butenedioate (1:1)
**: (E)—2-butenedioate (1:1)

4-[(2-benzothiazolyl)methylamino]-α-(4-methoxyphenyl)-1-piperidineethanol; mp. 168.1° C. (394);

4-[(2-benzothiazolyl)methylamino]-α-(4fluorophenyl)-1-piperidineethanol; mp. 178.5° C. (395);

3-[(2-benzothiazolyl)methylamino]-α-(phenoxymethyl)-8-azabicyclo[3.2.1]octane-8-ethanol ethanedioate(1:1); mp. 188.6° C. (396);

3-[(2-benzothiazolyl)methylamino]-α-[(4-fluorophenoxy)methyl]-1-piperidineethanol ethanedioate (1:1); mp. 182.7° C. (397);

3-[(2-benzothiazolyl)methylamino]-α-[(3-chlorophenoxy)methyl]-1-piperidineethanol ethanedioate (1:1); mp. 172.9° C. (398);

3-[(2-benzothiazolyl)methylamino]-α-(phenoxymethyl)-1-piperidineethanol ethanedioate (1:1); mp. 180.2° C. (399);

3-[(2-benzothiazolyl)methylamino]-α-[(3-chlorophenoxy)methyl]-1-pyrrolidineethanol ethanedioate(1:1); mp. 158.5° C. (400);

α-[(3-chlorophenoxy)methyl]-4-(thiazolo[5,4-b]-pyridin-2-ylamino)-1-piperidineethanol; mp. 127.4° C. (401);

(A)-4-(2-benzoxazolylamino)-α-(2,3-dihydro-1,4-benzodioxin-2-yl)-1-piperidineethanol dihydrochloride; mp. 229.8° C. (402);

(B)-4-(2-benzoxazolylamino)-α-(2,3-dihydro-1,4-benzodioxin-2-yl)-1-piperidineethanol dihydrochloride.hemihydrate; mp. 245.3° C. (403);

4-[(2-benzoxazolyl)methylamino]-α-(4-methoxyphenyl)-1-piperidineethanol dihydrochloride; mp. 231.1° C. (404);

3-[(2-benzothiazolyl)methylamino]-α-[(4-fluorophenoxy)methyl]-1-pyrrolidineethanol 4-methylbenzenesulfonate(1:2); mp. 199.8° C. (405);

α-[(4-fluorophenoxy)methyl]-4-[(1-methylthiazolo[5,4-b]pyridin-2-yliden)amino]-1-piperidineethanol; mp. 150.2° C. (406);

4-[(3-methyl-2(3H)-benzothiazolyiden)amino]-α-(phenoxymethyl)-1-piperidineethanol (Z)-2-butenedioate(1:2); mp. 152.8° C. (407);

4-[(2-benzothiazolyl)methylamino]-α-[[(2,4-dichlorophenyl)methoxy]methyl]-1-piperidineethanol ethanedioate(1:1); mp. 158.1° C. (408);

α-[(4-fluorophenoxy)methyl]-4-[(oxazolo[4,5-b]pyridin-2-yl)amino]-1-piperidineethanol (E)-2-butenedioate(1:1); mp. 195.4° C. (409);

(+)-(R)-4-[(2-benzothiazolyl)methylamino]-α-[(4-fluorophenoxy)methyl]-1-piperidineethanol dihydrochloride mp. 179.2° C., [α]= +12.49° (c=0.5% in methanol) (410); and (−)-(S)-4-[(2-benzothiazolyl)methylamino]-α-[(4-fluorophenoxy)methyl]-1-piperidineethanol dihydrochloride; mp. 175.7° C., [α]= −11.37° (c=0.5% in methanol) (411).

In a similar manner there is also prepared: α-[(4-fluorophenyl)methyl]-4-[(oxazolo[4,5-d]pyridin-2-yl)amino]-1-piperidineethanol (412).

EXAMPLE 34

A mixture of 2.7 parts of 2,3-dihydro-2-oxiranyl-1,4-benzodioxin, 3.5 parts of N-methyl-N-(4-piperidinyl)-2-benzoxazolamine, 45 parts of methylbenzene and 40 parts of methanol was stirred and refluxed overnight. The reaction mixture was evaporated and the residue was separated by column chromatography over Li-Chroprep. RP 18 using a mixture of water, ammonium acetate and methanol (30:0.5:70 by volume) as eluent. The first fraction (A-isomer) was collected and the eluent was evaporated. The residue was taken up in water and the solution was treated with sodium hydroxide. The product was extracted with trichloromethane. The extract was washed with water, dried, filtered and evaporated. The residue was crystallized from 2-propanol, yielding 0.3 parts (5%) of (A)-4-[(2-benzoxazolyl)methylamino]-α-(2,3-dihydro-1,4-benzodioxin-2-yl)-1-piperidineethanol; mp. 160.4° C. (413). The second fraction (B-isomer) was collected and the eluent was evaporated. The residue was taken up in water and the solution was treated with sodium hydroxide. The product was extracted with trichloromethane. The extract was washed with water, dried, filtered and evaporated. The residue was crystallized from a mixture of 2,2'-oxybispropane and methanol, yielding 1.3 parts (21%) of (B)-4-[(2-benzoxazolyl)methylamino]-α-(2,3-dihydro-1,4-benzodioxin-2-yl)-1-piperidineethanol; mp. 120.9° C. (414).

In a similar manner there were also prepared:

(A)-4-[(2-benzothiazolyl)methylamino]-α-(2,3-dihydro-1,4-benzodioxin-2-yl)-1-piperidineethanol; mp. 142.0° C. (415).

(B)-4-[(2-benzothiazolyl)methylamino]-α-(2,3-dihydro-1,4-benzodioxin-2-yl)-1-piperidineethanol; mp. 134.2° C. (416).

EXAMPLE 35

A mixture of 3.6 parts of [(3-chlorophenoxy)methyl]oxirane, 3.3 parts of N-methyl-N-(3-pyrrolidinyl)-2-benzoxazolamine and 90 parts of methylbenzene was stirred and refluxed overnight. The reaction mixture was evaporated. The residue was purified by column chromatography over silica gel using a mixture of trichloromethane and methanol (99:1 by volume) as eluent. The pure fractions were collected and the eluent was evaporated. The residue was converted into the 4-methylbenzenesulfonate salt in 2-propanol. The salt was filtered off and dried, yielding 5 parts (58%) of 3-[(2-benzoxazolyl)methylamino]-α-[(3-chlorophenoxy)methyl]-1-pyrrolidineethanol 4-methylbenzenesulfonate(1:1); mp. 96.8° C. (417).

In a similar manner there were also prepared:

4-[(2-benzothiazolyl)methylamino]-α-[(3-fluorophenoxy)methyl-1-piperidineethanol dihydrochloride; mp. 205.2° C. (418).

4-[(2-benzothiazolyl)(phenylmethyl)amino]-α-[(4-fluorophenoxy)methyl]-1-piperidineethanol (E)-2-butenedioate(2:1); mp. 163.5° C. (419);

4-[methyl(6-methyl-2-benzothiazolyl)amino]-α-(phenoxymethyl)-1-piperidineethanol; mp. 140.6° C. (420);

α-[(4-fluorophenoxy)methyl]-4-[methyl(6-methyl-2-benzothiazolyl)amino]-1-piperidineethanol; mp. 105.5° C. (421);

α-[(3-fluorophenoxy)methyl]-4-[methyl(6-methyl-2-benzothiazolyl)amino]-1-piperidineethanol; mp. 109.6° C. (422);

4-[(2-benzothiazolyl)(phenylmethyl)amino]-α-[(4-chlorophenoxy)methyl]-1-piperidineethanol (E)-2-butenedioate(2:1); mp. 172.0° C. (423);

4-[(2-benzothiazolyl)methylamino]-α-[(4-fluorophenoxy)methyl]-α-methyl-1-piperidineethanol 4-methylbenzenesulfonate(1:2); mp. 207.3° C. (424);

cis-4-[(2-benzothiazolyl)methylamino]-3-hydroxy-α-(phenoxymethyl)-1-piperidineethanol; mp. 152.2° C. (425);

cis-4-[(2-benzothiazolyl)amino]-α-[(4-fluorophenoxy)-methyl]-3-hydroxy-1-piperidineethanol (Z)-2-butenedioate(1:2); mp. 156.7° C. (426); and
4-[(2-benzothiazolyl)methylamino]-α-[[(2,3-dihydro-1,4-benzodioxin-2-yl)-methoxy]methyl]-1-piperidineethanol (E)-2-butenedioate(1:1); mp. 146.5° C. (427).

EXAMPLE 36

A mixture of 2.77 parts of [(3-chlorophenoxy)methyl]oxirane, 4.92 parts of N-(3-methyl-2(3H)-benzothiazolylidene)-4-piperidinamine monohydrobromide, 2.12 parts of sodium carbonate, 60 parts of methanol and 68 parts of methylbenzene was stirred and refluxed overnight. The reaction mixture was cooled and the solvent was evaporated. The residue was purified by filtration over silica gel using a mixture of trichloromethane and methanol (99:1 by volume), as eluent. The pure fractions were collected and the eluent was evaporated. The residue was converted into the (Z)-2-butenedioate salt in 2-propanol and methanol. The salt was filtered off and dried, yielding 5.5 parts (55%) of α-[(3-chlorophenoxy)methyl]-4-[(3-methyl-2(3H)-benzothiazolyliden)amino]-1-piperidineethanol (Z)-2-butenedioate(1:2); mp. 157.6° C. (428).

In a similar manner there were also prepared:
α-[(4-fluorophenoxy)methyl]-4-[(3-methyl-2(3H)-benzothiazolyliden)amino]-1-piperidineethanol (Z)-2-butenedioate (1:2); mp. 140.2° C. (429); and
3-[(2-benzothiazolyl)methylamino]-α-(phenoxymethyl)-1-pyrrolidineethanol 4-methylbenzenesulfonate(1:2); mp. 196.3° C. (430).

EXAMPLE 37

A mixture of 2.5 parts of [(4-fluorophenoxy)methyl]oxirane, 4.3 parts of N-butyl-N-(4-piperidinyl)-2-benzothiazolamine, 45 parts of benzene and 40 parts of methanol was stirred and refluxed overnight. The reaction mixture was evaporated. The residue was purified by column chromatography over silica gel using a mixture of trichloromethane and methanol (97:3 by volume) as eluent. The pure fractions were collected and the eluent was evaporated. The residue was converted into the (E)-2-butenedioate salt in ethanol. The salt was filtered off and dried, yielding 5.6 parts (72%) of 4-[(2-benzothiazolyl)butylamino]-α-[(4-fluorophenoxy)methyl]-1-piperidineethanol (E)-2-butenedioate(2:1); mp. 196.8° C. (431).

In a similar manner there were also prepared: 4-[(2-benzothiazolyl)butylamino]-α-[(4-chlorophenoxy)methyl]-1-piperidineethanol (E)-2-butenedioate(2:1); mp. 192.2° C. (432).

EXAMPLE 38

A mixture of 1.8 parts of (B)-3,4-dihydro-2-oxiranyl-2H-1-benzopyran, 2.3 parts of N-methyl-N-(4-piperidinyl)-2-benzoxazolamine and 40 parts of ethanol was stirred and refluxed overnight. The reaction mixture was evaporated. The oily residue was purified by column chromatography over silica gel using a mixture of trichloromethane and methanol (90:10by volume) as eluent. The pure fractions were collected and the eluent was evaporated. The oily residue was converted into the ethanedioate salt in 2-propanol. The salt was filtered off (slowly), washed with 2-propanol and 2,2'-oxybispropane and dried, yielding 3.82 parts (77.6%) of (B)-4-[(2-benzoxazolyl)methylamino]-α-(3,4-dihydro-2H-1-benzopyran-2-yl)-1-piperidineethanol ethanedioate (1:1); mp. 192.5° C. (433).

Following the same procedure and using equivalent amounts of the appropriate starting materials, there were also prepared:
(A)-4-[(2-benzothiazolyl)methylamino]-α-(3,4-dihydro-2H-1-benzopyran-2-yl)-1-piperidineethanol ethanedioate(1:1); mp. 195.0° C. (434);
(B)-4-[(2-benzothiazolyl)methylamino]-α-(3,4-dihydro-2H-1-benzopyran-2-yl)-1-piperidineethanol; mp. 133.4° C. (435);
(A)-4-[(2-benzoxazolyl)methylamino]-α-(3,4-dihydro-2H-1-benzopyran-2-yl)-1-piperidineethanol ethanedioate (1:1); mp. 206.0° C. (436);
A+-4-[(2-benzothiazolyl)methylamino]-α-(3,4-dihydro-2H-1-benzopyran-2-yl)-1-piperidineethanol ethanedioate(2:5); mp. 159.0° C. (437);
(A−)-4-[(2-benzothiazolyl)methylamino]-α-(3,4-dihydro-2H-1-benzopyran-2-yl)-1-piperidineethanol; mp. 186.3° C.; $[\alpha]^D = -4.61°$ (c=1% in methanol) (438); and
A+-4-[(2-benzothiazolyl)methylamino]-α-(3,4-dihydro-2H-1-benzopyran-2-yl)-1-piperidineethanol; mp. 138.5° C.; $[\alpha]^{25} = 47.60°$ (c=1% in methanol) (439).

EXAMPLE 39

A mixture of 3.7 parts of [(phenylthio)methyl]oxirane, 5.0 parts of N-methyl-N-(4-piperidinyl)-2-benzothiazolamine and 120 parts of 2-propanol was stirred overnight at reflux temperature. The reaction mixture was evaporated. The residue was converted into the (Z)-2-butenedioate salt in 2-propanol and 2,2'-oxybispropane (5:1 by volume). The salt was filtered off and dried, yielding 8.3 parts (78.3%) of 4-[(2-benzothiazolyl)methylamino]-α-[(phenylthio)methyl]-1-piperidineethanol (Z)-2-butenedioate(1:1); mp. 160.2° C. (440).

In a similar manner there were also prepared:
4-[(2-benzothiazolyl)methylamino]-α-[(2-bromo-4-fluorophenoxy)methyl]-1-piperidineethanol; mp. 124.6° C. (441);
4-[(2-benzothiazolyl)methylamino]-α-[[(4-fluorophenyl)thio]methyl]-1-piperdineethanol (Z)-2-butenedioate(1:1); mp. 140.6° C. (442);
4-[(2-benzothiazolyl)methylamino]-α-[[(4-chlorophenyl)thio]methyl]-1-piperidineethanol (Z)-2-butenedioate(1:1); mp. 174.1° C. (443);
4-[(2-benzoxazolyl)methylamino]-α-[[(4-fluorophenyl)thio]methyl]-1-piperidineethanol (Z)-2-butenedioate(1:1); mp. 141.7° C. (444);
4-[(2-benzoxazolyl)methylamino]-α-[[(4-chlorophenyl)thio]methyl]-1-piperidineethanol (Z)-2-butenedioate(1:1); mp. 168.8° C. (445);
4-[(2-benzoxazolyl)methylamino]-α-[(phenylthio)methyl]-1-piperidineethanol (E)-2-butenedioate(2:1); mp. 180.2° C. (446); and
α-[(4-fluorophenoxy)methyl]-4-[(thiazolo[4,5-c]pyridin-2-yl)amino]-1-piperidineethanol ethanedioate(1:2); mp. 195.9° C. (447).

EXAMPLE 40

A mixture of 1.65 parts of 1-(4-fluorobenzoyl)aziridine (solution in benzene 1.2M), 2.1 parts of N-(4-piperidinyl)-2-benzoxazolamine and 90 parts of methylbenzene was stirred and refluxed overnight. The reaction mixture was evaporated and the residue was crystallized from 2-propanol. The product was filtered off and recrystallized from 2-propanone, yielding 1.3 parts (34%) of N-[2-[4-[(2-benzoxazolyl)amino]-1-piperidinyl]ethyl]-4-fluorobenzamide; mp. 173.3° C. (448).

In a similar manner there were also prepared: N-[2-[4-[2-(benzoxazolyl)methylamino]-1-piperidinyl]ethyl]-4-fluorobenzamide; mp. 162.9° C. (449).

EXAMPLE 41

A mixture of 3.2 parts of 4-(1-ethenyl)pyridine, 2.1 parts of N-(4-piperidinyl)-2-benzoxazolamine and 80 parts of 1-butanol was stirred and refluxed for 48 hours. The reaction mixture was evaporated. The residue was purified by column chromatography over silica gel using a mixture of trichloromethane and methanol (97:3 by volume) saturated with ammonia, as eluent. The pure fractions were collected and the eluent was evaporated. The residue was crystallized from 2,2'-oxybispropane, yielding 2 parts (62%) of N-[1-[2-(4-pyridinyl)ethyl]-4-piperidinyl]-2-benzoxazolamine; mp. 146.9° C. (450).

In a similar manner there were also prepared:
N-[1-[2-(2-pyridinyl)ethyl]-4-piperidinyl]-2-benzoxazolamine; mp. 130° C. (451); and
N-methyl-N-[1-[2-(2-pyridinyl)ethyl]-4-piperidinyl]-2-benzoxazolamine; mp. 102.3° C. (452).

EXAMPLE 42

A mixture of 4.2 parts of 4-[(2-benzothiaolyl)methylamino]-α-[(4-fluorophenoxy)methyl]-1-piperidineethanol. 4.1 parts of acetic acid anhydride, 0.1 parts of 4-methylbenzenesulfonic acid and 135 parts of methylbenzene was stirred and refluxed overnight. After cooling to room temperature, the reaction mixture was washed with a sodium hydroxide solution 5% and with water, dried, filtered and evaporated. The residue was crytallized from 2,2'-oxybispropane. The product was filtered off and dried, yielding 3.5 parts (77%) of 4-[(2-benzothiazolyl)methylamino]-α-[(4-fluorophenoxy)methyl]-1-piperidineethanol acetate(ester); mp. 100.0° C. (453).

EXAMPLE 43

To a stirred and hot (60° C.) solution of 4.2 parts of 4-[(2-benzothiazolyl)methylamino]-α-[(4-fluorophenoxy)methyl]-1-piperidineethanol in 90 parts of N,N-dimethylformamide were added dropwise 2.3 parts of decanoyl chloride. Upon completion, stirring was continued for 24 hours at 60° C. After cooling to room temperature, the reaction mixture was poured onto water and the whole was treated with sodium hydroxide. The aqueous phase was decanted and the residual product was washed three times with water and dissolved in trichloromethane. The organic layer was dried, filtered and evaporated. The residue was purified by column chromatography over silica gel using a mixture of trichloromethane and methanol (97:3 by volume) as eluent. The pure fractions were collected and the eluent was evaporated. The residue was converted into the (Z)-2-butenedioate salt in a mixture of 2-propanone and 2,2'-oxybispropane. The salt was filtered off and dried, yielding 1.1 parts (16%) of [2-[4-[(2-benzothiazolyl)methylamino]-1-piperidinyl]-1-[(4-fluorophenoxy)methyl]ethyl]decanoate (Z)-2-butenedioate(1:1); mp. 134.2° C. (454).

EXAMPLE 44

3.4 Parts of (cis+trans)-N-[1-[4-(4-fluorophenoxy)cyclohexyl]-4-piperidinyl]-N-methyl-2-benzothiazolamine were separated by column chromatography (HPLC) over silica gel using a mixture of trichloromethane and methanol (98:2 by volume) as eluent.

The first fraction (A-isomer) was collected and the eluent was evaporated. The residue was crystallized from 2-propanol, yielding 0.34 parts of (A)-N-[1-[4-(4-fluorophenoxy)cyclohexyl]-4-piperidinyl]-N-methyl-2-benzothiazolamine; mp. 155.5° C. (455).

The second fraction (B-isomer) was collected and the eluent was evaporated. The residue was crystallized from 2-propanol, yielding 0.34 parts of (B)-N-[1-[4-(4-fluorophenoxxy)cyclohexyl]-4-piperidinyl]-N-methyl-2-benzothiazolamine; mp. 116.5° C. (456).

EXAMPLE 45

To a stirred solution of 5 parts of 4-[(2-benzothiazolyl)methylamino]-α-[(4-fluorophenoxy)methyl]-1-piperidineethanol in 80 parts of ethanol were added 1.8 parts of (+)-[R-(R*,R*)]-2,3-dihydroxybutanedioic acid while boiling. The product was allowed to crystallize. It was filtered off and dried, yielding 5.5 parts (94%) of (+)-4-[(2-benzothiazolyl)methylamino]-α-[(4-fluorophenoxy)methyl]-1-piperidineethanol [R-(R*,R*)]-2,3-dihydroxybutanedioate (2:1); mp. 189.1° C. (457).

In a similar manner there were also prepared:
4-[(2-benzothiazolyl)methylamino]-α-[(4-fluorophenoxy)methyl]-1-piperidineethanol 2-hydroxy-1,2,3-propanetricarboxylate(1:1); mp 146.7° C.; (458) and
4-[(2-benzothiazolyl)methylamino]-α-[(4-fluorophenoxy)methyl]-1-piperidineethanol (Z)-2-butenedioate (1:1); mp. 127.6° C. (459).

C. Pharmacological Examples

The useful anti-anoxic properties of the compounds of formula (I) can be demonstrated in the following test procedures.

EXAMPLE 46

KCN Test in Rats

Histotoxic anoxia is produced by a rapid intravenous injection of potassium cyanide (KCN) in rats.

KCN in control rats induces abdominal contractions and clonic seizures and is lethal within 2 minutes. The protection from KCN induced lethality appears to be a simple way of evaluating quantitatively the anti-anoxic properties of the test compounds. Male Wistar rats weighing ±200 g were treated subcutaneously with a test compound. One hour after treatment there was injected intravenously a KCN solution at a dose of 5 mg/kg body weight. Survival after 2 minutes was evaluated and $ED_{50}$-values were determined.

The $ED_{50}$-values of the compounds of formula (I) are listed in table I. Said $ED_{50}$-values are those values in mg/kg body weight capable of protecting 50% of the tested animals against KCN-induced lethality.

The compounds listed in table 1 are not given for the purpose of limiting the invention thereto but only to exemplify the useful pharmacological activities of all the compounds within the scope of formula (I).

| Compound number | $ED_{50}$-values in mg/kg body weight |
|---|---|
| 1 | 5 |
| 9 | 2.5 |
| 10 | 5 |
| 11 | 1.25 |
| 15 | 0.63 |

-continued

| Compound number | ED$_{50}$-values in mg/kg body weight |
| --- | --- |
| 18 | 5 |
| 24 | 5 |
| 31 | 5 |
| 32 | 5 |
| 42 | 2.5 |
| 48 | 1.25 |
| 50 | 2.5 |
| 75 | 10 |
| 103 | 5 |
| 107 | 2.5 |
| 108 | 5 |
| 118 | 5 |
| 120 | 2.5 |
| 121 | 2.5 |
| 123 | 5 |
| 133 | 5 |
| 146 | 5 |
| 148 | 5 |
| 151 | 5 |
| 184 | 5 |
| 191 | 2.5 |
| 195 | 1.25 |
| 309 | 5 |
| 320 | 1.8 |
| 322 | 5 |
| 323 | 1.25 |
| 324 | 2.5 |
| 357 | 0.63 |
| 405 | 10 |
| 410 | 5 |
| 411 | 5 |
| 413 | 5 |
| 415 | 10 |
| 438 | 10 |
| 440 | 10 |
| 442 | 2.5 |
| 443 | 10 |
| 446 | 10 |
| 452 | 5 |

(D) Composition Examples

The following formulations exemplify typical pharmaceutical compositions in dosage unit form suitable for systemic administration to animal and human subjects in accordance with the instant invention.

"Active ingredient" (A.I.) as used throughout these examples relates to a compound of formula (I) or pharmaceutically acceptable acid addition salt thereof.

EXAMPLE 47

Oral Drops

500 Grams of the A.I. was dissolved in 0.5 liters of 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

EXAMPLE 48

Oral Solution

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

EXAMPLE 49

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

EXAMPLE 50

Film-Coated Tablets

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10,000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 millliters of dichloromethane. Then there were added 75 milliliters of dichloromethane and 2.5 milliliters 1,2,3-propanetriol. 10 Grams of polyethylene glycol was molten and dissolvd in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated. The tablet cores were coated with the thus obtained mixture in a coating apparatus.

EXAMPLE 51

Injectable Solution 1.8 Gram methyl 4--hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 52

Suppositories

3 Grams A.I. was dissolved in a solution of 3 grams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. the latter mixture was mixed well with the former solution. The thus obtained mixture was poured into moulds at a temperature of 37°-38° C. to form 100 suppositories each containing 30 milligrams of the active ingredient.

What we claim is:

1. A chemical compound having the formula

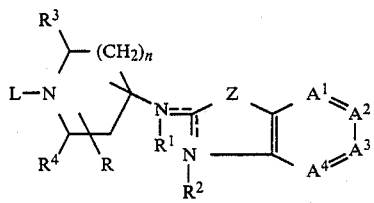
(I)

a pharmaceutically acceptable acid addition salt or a possible stereochemically isomeric form thereof, wherein:

—$A^1$=$A^2$—$A^3$=$A^4$— is a bivalent radical having the formula

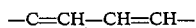 (a);

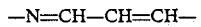 (b);
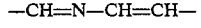 (c);

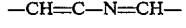 (d); or

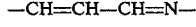 (e);

wherein
one or two hydrogen atoms in the radical —$A^1$=$A^2$—$A^3$=$A^4$— may, each independently from each other, be replaced by halo, $C_{1-6}$ alkyl, hydroxy, $C_{1-6}$ alkyloxy or trifluoromethyl;
Z is O or S;
n is 0 or the integer 1;
R is a member selected from the group consisting of hydrogen, $C_{1-6}$ alkyl, hydroxy and $C_{1-6}$ alkyloxy or trifluoromethyl;
$R^1$ or $R^2$ is hydrogen, $C_{1-6}$ alkyl, or Ar $C_{1-6}$ alkyl; the dotted line between the nitrogen atom bearing $R^1$, the interjacent carbon atom and the nitrogen atom bearing $R^2$ indicating that a double bond exists between the nitrogen bearing $R^1$ and said interjacent carbon atom, in which case $R^1$ is absent, or a double bond exists between the interjacent carbon and the nitrogen bearing $R^2$, in which case $R^2$ is absent; and wherein said interjacent carbon atom is the carbon atom positioned between the nitrogen bearing $R^1$ and the nitrogen bearing $R^2$;
$R^3$ or $R^4$ are both hydrogens or $R^3$ and $R^4$ combined may form a bivalent radical of formula —$CH_2$—$CH_2$—;
L is a member selected from the group consisting of $C_{1-12}$ alkyl, substituted $C_{1-6}$ alkyl, Ar $C_{2-6}$ alkenyl, $C_{3-6}$ cycloalkyl, substituted $C_{3-6}$ cycloalkyl, a radical of formula

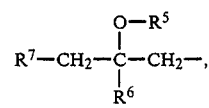 (a)

and a radical of formula

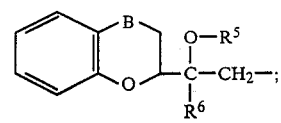 (b)

$R^5$ being hydrogen or $C_{1-12}$ alkylcarbonyl;
$R^6$ being hydrogen or $C_{1-6}$ alkyl;
$R^7$ being Ar, a radical $R^8$-O or a radical $R^8$-S;
B being a bivalent radical of formula —$CH_2$— or —O—; and
said $R^8$ being hydrogen; Ar; 2,3-dihydro-1H-indenyl; benzodioxolyl; (2,3-dihydro-1,4-benzodioxin-2-yl)methyl; (2H-1-benzopyran-2-yl)methyl; or phenyl substituted with $C_{2-6}$-alkenyloxy, $C_{1-6}$ alkylcarbonylamino or $C_{1-6}$ alkylphenylcarbonyl; and
wherein said substituted $C_{3-6}$ cycloalkyl is $C_{3-6}$ cycloalkyl being substituted with up to two substitutents each independently selected from the group consisting of aryl, aryloxy and cyano;
said substituted $C_{1-6}$ alkyl is $C_{1-6}$ alkyl being substituted with a member selected from the group consisting of $C_{3-6}$ cycloalkyl, pyridinyl, pyridinyloxy, Ar, benzimidazolyl, indolyl, isoxazolyl being optionally substituted with phenyl, 3-oxo-1,2,4-triazolo[4,5-a]-pyridin-2(3H)-yl, a radical of formula ArY—, a radical of formula $R^9$O— and a radical of formula

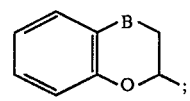 (c)

Y being O, S, NH, —CONH—,

$R^9$ being hydrogen, Ar $C_{1-6}$ alkyl, $C_{3-6}$ cycloalkyl, phenyl substituted with phenyl, or phenyl substituted with $C_{1-6}$ alkyloxycarbonyl;
$R^{10}$ being hydrogen or $C_{1-6}$ alkyl; and
wherein Ar is phenyl optionally substituted with up to three substituents each independently selected from the group consisting of $C_{1-6}$ alkyl, $C_{1-6}$ alkyloxy, halo, trifluoromethyl, cyano, $C_{1-6}$ alkylcarbonyl, nitro, amino and aminocarbonyl.

2. A chemical compound according to claim 1, wherein L is Ar $C_{2-6}$ alkenyl, $C_{1-6}$ alkyl being substituted with aryloxy, a radical of formula (a) or a radical of formula (b).

3. A chemical compound according to claim 2, wherein —$A^1$=$A^2$—$A^3$=$A^4$— is —CH=CH—C=CH—, n is the integer 1, $R^2$ is absent and a double bond exists between the nitrogen bearing $R^2$ and the interjacent carbon atom, and $R^3$ and $R^4$ are both hydrogen atoms.

4. A chemical compound according to claim 3 wherein in the radical of formula (a), $R^5$ and $R^6$ are both hydrogen and $R^7$ is a radical $R^8$—O—, wherein $R^8$ is Ar; or wherein in the radical of formula (b), B is O and $R^5$ and $R^6$ are both hydrogen radicals.

5. A chemical compound according to claim 4 wherein $R^1$ is $C_{1-6}$ alkyl and Ar is halophenyl.

6. A chemical compound according to claim 1, wherein the compound is 4-[(2-benzothiazolyl)methylamino]-α-[(4-fluorophenoxy)methyl]-1-piperidineethanol.

7. An anti-anoxic composition comprising a pharmaceutically acceptable carrier and as active ingredient an anti-anoxic effective amount of a compound of formula

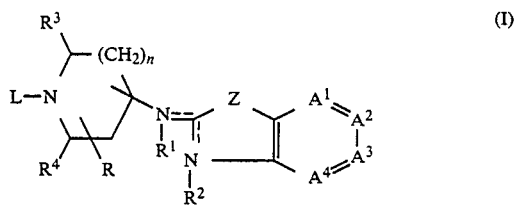

a pharmaceutically acceptable acid addition salt or a possible stereochemically isomeric form thereof, wherein:

—$A^1$=$A^2$—$A^3$=$A^4$— is a bivalent radical having the formula

 —CH=CH—CH=CH— (a);

 —N=CH—CH=CH— (b);

 —CH=N—CH=CH— (c);

 —CH=CH—N=CH— (d); or

 —CH=CH—CH=N— (e);

wherein one or two hydrogen atoms in the radical —$A^1$=$A^2$—$A^3$=$A^6$— may, each independently from each other, be replaced by halo, $C_{1-6}$ alkyl, hydroxy, $C_{1-6}$ alkyloxy, or trifluoromethyl;

Z is O or S;
n is 0 or the integer 1;
R is a member selected from the group consisting of hydrogen, $C_{1-6}$ alkyl, hydroxy and $C_{1-6}$ alkyloxy;
$R^1$ or $R^2$ is hydrogen, $C_{1-6}$ alkyl, or Ar $C_{1-6}$ alkyl; the dotted line between the nitrogen atom bearing $R^1$, the interjacent carbon atom and the nitrogen atom bearing $R^2$ indicating that a double bond exists between the nitrogen bearing $R^1$ and said interjacent carbon atom, in which case $R^1$ is absent, or a double bond exists between the interjacent carbon and the nitrogen bearing $R^2$, in which case $R^2$ is absent; and wherein said interjacent carbon atom is the carbon atom positioned between the nitrogen bearing $R^1$ and the nitrogen bearing $R^2$;
$R^3$ or $R^4$ are both hydrogens or $R^3$ and $R^4$ combined may form a bivalent radical of formula —CH$_2$—CH$_2$—;
L is a member selected from the group consisting of $C_{1-12}$ alkyl, substituted $C_{1-6}$ alkyl, Ar $C_{2-6}$ alkenyl, $C_{3-6}$ cycloalkyl, substituted $C_{3-6}$ cycloalkyl, a radical of formula

and a radical of formula

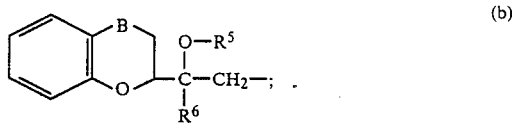

$R^5$ being hydrogen or $C_{1-12}$ alkylcarbonyl;
$R^6$ being hydrogen or $C_{1-6}$ alkyl;
$R^7$ being Ar, a radical $R^8$—O or a radical $R^8$—S;
B being a bivalent radical of formula —CH$_2$— or —O—; and
said $R^8$ being hydrogen; Ar; 2,3-dihydro-1H-indenyl; benzodioxolyl; (2,3-dihydro-1,4-benzodioxin-2-yl)methyl; (2H-1-benzopyran-2-yl)methyl; or phenyl substituted with $C_{2-6}$alkenyl oxy, $C_{1-6}$ alkylcarbonylamino or $C_{1-6}$ alkylphenylcarbonyl; and
wherein said substituted $C_{3-6}$ cycloalkyl is $C_{3-6}$ cycloalkyl being substituted with up to two substituents each independently selected from the group consisting of aryl, aryloxy and cyano;
said substituted $C_{1-6}$ alkyl is $C_{1-6}$ alkyl being substituted with a member selected from the group consisting of $C_{3-6}$ cycloalkyl, pyridinyl, pyridinyloxy, Ar, benzimidazolyl, indolyl, isoxazolyl being optionally substituted with phenyl, 3-oxo-1,2,4-triazolo[4,5-a]pyridin-2(3H)-yl, a radical of formula ArY—, a radical of formula $R^9$O— and a radical of formula

Y being O, S, NH, —CONH—,

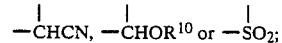 —CHCN, —CHOR$^{10}$ or —SO$_2$;

$R^9$ being hydrogen, Ar $C_{1-6}$ alkyl, $C_{3-6}$ cycloalkyl, phenyl substituted with phenyl, or phenyl substituted with $C_{1-6}$ alkyloxycarbonyl;
$R^{10}$ being hydrogen or $C_{1-6}$ alkyl; and
wherein aryl is phenyl optionally substituted with up to three substituents each independently selected from the group consisting of $C_{1-6}$ alkyl, $C_{1-6}$ alkyloxy, halo, trifluoromethyl, cyano, $C_{1-6}$ alkylcarbonyl, nitro, amino and aminoarbonyl.

8. An anti-anoxic composition according to claim 7, wherein L is Ar $C_{2-6}$ alkenyl, $C_{1-6}$ alkyl being substituted with aryloxy, with a radical of formula (a) or with a radical of formula (b).

9. An anti-anoxic composition according to claim 8, wherein —$A^1$=$A^2$—$A^3$=$A^4$— is CH=CH—CH=CH—, n is the integer 1, $R^2$ is absent and a double bond exists between the nitrogen bearing $R^2$ and the interjacent carbon atom, and $R^3$ and $R^4$ are both hydrogen atoms.

10. An anti-anoxic composition according to claim 9, wherein in the radical of formula (a), $R^5$ and $R^6$ are both hydrogen and $R^7$ is a radical $R^8$—O—, wherein $R^8$ is Ar; or wherein in the radical of formula (b), B is O and $R^5$ and $R^6$ are both hydrogen radicals.

11. An anti-anoxic composition according to claim 10, wherein $R^1$ is $C_{1-6}$ alkyl and Ar is halophenyl.

12. An anti-anoxic composition according to claim 7, wherein the compound is 4-[(2-benzothiazolyl)methylamino]-α-[(4-fluorophenoxy)methyl]-1-piperidineethanol.

13. A method of treating warm-blooded animals suffering from anoxia which method comprises the systemic administration to warm-blooded animals of an anti-anoxic effective amount of a compound having the formula

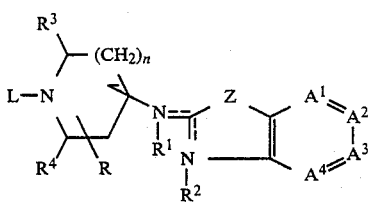   (I)

a pharmaceutically acceptable acid addition salt or a possible stereochemically isomeric form thereof, wherein:

—$A^1$=$A^2$—$A^3$=$A^4$— is a bivalent radical having the formula

—CH=CH—CH=CH— (a);

—N=CH—CH=CH— (b);

—CH=N—CH=CH— (c);

—CH=CH—N=CH— (d); or

—CH=CH—CH=N— (e);

wherein one or two hydrogen atoms in the radical —$A^1$=$A^2$—$A^3$=$A^4$— may, each independently from each other, be replaced by halo, $C_{1-6}$ alkyl, hydroxy, $C_{1-6}$ alkyloxy, or trifluoromethyl;

Z is O or S;

n is 0 or the integer 1;

R is a member selected from the group consisting of hydrogen, $C_{1-6}$ alkyl, hydroxy and $C_{1-6}$ akyloxy;

$R^1$ or $R^2$ is hydrogen, $C_{1-6}$ alkyl, or Ar $C_{1-6}$ alkyl; the dotted line between the nitrogen atom bearing $R^1$, the interjacent carbon atom and the nitrogen atom bearing $R^2$ indicating that a double bond exists between the nitrogen bearing $R^1$ and said interjacent carbon atom, in which case $R^1$ is absent, or a double bond exists between the interjacent carbon and the nitrogen bearing $R^2$, in which case $R^2$ is absent; and wherein said interjacent carbon atom is the carbon atom positioned between the nitrogen bearing $R^1$ and the nitrogen bearing $R^2$;

$R^3$ or $R^4$ are both hydrogens or $R^3$ and $R^4$ combined may form a bivalent radical of formula —CH$_2$—CH$_2$—;

L is a member selected from the group consisting of $C_{1-12}$ alkyl, substituted $C_{1-6}$ alkyl, Ar $C_{2-6}$ alkenyl, $C_{3-6}$ cycloalkyl, substituted $C_{3-6}$ cycloalkyl, a radical of formula

and a radical of formula

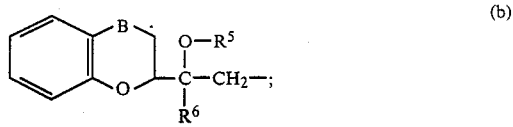

$R^5$ being hydrogen or $C_{1-12}$ alkylcarbonyl;

$R^6$ being hydrogen or $C_{1-6}$ alkyl;

$R^7$ being Ar, a radical $R^8$—O or a radical $R^8$—S;

B being a bivalent radical of formula —CH$_2$— or —O—; and said $R^8$ being hydrogen; Ar; 2,3-dihydro-1H-indenyl; benzodioxolyl; (2,3-dihydro-1,4-benzodioxin-2-yl)methyl; (2H-1-benzopyran-2-yl)methyl; or phenyl substituted with $C_{2-6}$ alkenyloxy, $C_{1-6}$ alkylcarbonylamino or $C_{1-6}$ alkylphenylcarbonyl; and wherein said substituted $C_{3-6}$ cycloalkyl is $C_{3-6}$ cycloalkyl being substituted with up to two substituents each independently selected from the group consisting of aryl, aryloxy and cyano;

said substituted $C_{1-6}$ alkyl is $C_{1-6}$ alkyl being substituted with a member selected from the group consisting of $C_{3-6}$ cycloalkyl, pyridinyl, pyridinyloxy, Ar, benzimidazolyl, indolyl, isoxazolyl being optionally substituted with phenyl, 3-oxo-1,2,4-triazolo[4,5-a]-pyridin-2(3H)-yl, a radical of formula ArY—, a radical of formula $R^9$O— and a radical of formula

Y being O, S, NH, —CONH—,

$R^9$ being hydrogen, Ar $C_{1-6}$ alkyl, $C_{3-6}$ cycloalkyl, phenyl substituted with phenyl, or phenyl substituted with $C_{1-6}$ alkyloxycarbonyl;

$R^{10}$ being hydrogen or $C_{1-6}$ alkyl; and wherein Ar is phenyl optionally substituted with up to three substituents each independently selected from the group consisting of $C_{1-6}$ alkyl, $C_{1-6}$ alkyloxy, halo, trifluoromethyl, cyano, $C_{1-6}$ alkylcarbonyl, nitro, amino and aminocarbonyl.

14. A method according to claim 13, wherein L is Ar $C_{1-6}$ alkenyl, $C_{1-6}$ alkyl being substituted with aryloxy, with a radical of formula (a) or with a radical of formula (b).

15. A method according to claim 14, wherein A is —$A^1$=$A^2$—$A^3$=$A^4$— is —CH=CH—CH=CH—, n is the integer 1, $R^2$ is absent and a double bond exists between the nitrogen bearing $R^2$ and the interjacent carbon atom, and $R^3$ and $R^4$ are both hydrogen atoms.

16. A method according to claim 15, wherein in the radical of formula (a), $R^5$ and $R^6$ are both hydrogen and $R^7$ is a radical $R^8$—O—, wherein $R^8$ is Ar; or wherein in the radical of formula (b), B is O and $R^5$ and $R^6$ are both hydrogen radicals.

17. A method according to claim 16, wherein $R^1$ is $C_{1-6}$ alkyl and Ar is halophenyl.

18. A method according to claim 13, wherein the compound is 4-[(2-benzothiazolyl)methylamino]-α-[(4-fluorophenoxy)methyl]-1-piperidineethanol.

* * * * *

UNITED STATES PATENT AND TRADEMARK OFFICE
CERTIFICATE OF CORRECTION

PATENT NO. : 4,861,785

DATED : Aug. 29, 1989

INVENTOR(S) : Raymond A. Stokbroekx, et al.

It is certified that error appears in the above-identified patent and that said Letters Patent is hereby corrected as shown below:

Claim 1, Col. 53, line 37 "-CH=C-N=CH-(d); or" should read:
-- -CH=CH-N=CH-(d); or --.

Claim 7, Col. 55, line 43 "$-A^1=A^2-A^3=A_6-$" should read:
-- $-A^1=A^2-A^3=A^4-$ --.

Claim 7, Col. 56, line 58 "aminoarbonyl" should read:
-- aminocarbonyl --.

Claim 9, Col. 56, line 64 "CH=CH-CH=CH-" should read:
-- -CH=CH-CH=CH- --.

Signed and Sealed this

Eighteenth Day of September, 1990

Attest:

HARRY F. MANBECK, JR.

Attesting Officer     Commissioner of Patents and Trademarks